United States Patent
Mizobe et al.

(10) Patent No.: US 9,398,269 B2
(45) Date of Patent: Jul. 19, 2016

(54) MEDICAL SUPPORT SYSTEM

(71) Applicant: CANON KABUSHIKI KAISHA, Tokyo (JP)

(72) Inventors: Hideaki Mizobe, Tokyo (JP); Kazushige Hatori, Saitama (JP)

(73) Assignee: Canon Kabushiki Kaisha, Tokyo (JP)

( * ) Notice: Subject to any disclaimer, the term of this patent is extended or adjusted under 35 U.S.C. 154(b) by 476 days.

(21) Appl. No.: 13/859,178

(22) Filed: Apr. 9, 2013

(65) Prior Publication Data

US 2013/0293694 A1  Nov. 7, 2013

(30) Foreign Application Priority Data

Apr. 12, 2012 (JP) .................................. 2012-091250
Feb. 20, 2013 (JP) .................................. 2013-030899

(51) Int. Cl.
*H04N 7/18* (2006.01)
*G06F 19/00* (2011.01)

(52) U.S. Cl.
CPC .............. *H04N 7/183* (2013.01); *G06F 19/321* (2013.01); *G06F 19/3418* (2013.01)

(58) Field of Classification Search
CPC .... A61B 5/742; A61B 5/0013; G06F 15/173; H04N 7/183
See application file for complete search history.

(56) References Cited

U.S. PATENT DOCUMENTS

| | | | |
|---|---|---|---|
| 2004/0190781 A1* | 9/2004 | Shiibashi et al. | 382/210 |
| 2005/0251020 A1 | 11/2005 | Kondo et al. | |
| 2007/0016686 A1* | 1/2007 | Hollebeek et al. | 709/238 |
| 2008/0049901 A1 | 2/2008 | Tamakoshi | |

FOREIGN PATENT DOCUMENTS

| | | |
|---|---|---|
| JP | 11312200 A | 11/1999 |
| JP | 2000244694 A | 9/2000 |
| JP | 2004164320 A | 6/2004 |
| WO | 2007049471 A1 | 5/2007 |

* cited by examiner

*Primary Examiner* — Joseph Ustaris
*Assistant Examiner* — Zhubing Ren
(74) *Attorney, Agent, or Firm* — Canon USA Inc. IP Division

(57) ABSTRACT

There is provided a medical support system in which a plurality of photography apparatuses and a portable-type viewer apparatus including a display unit are communicably connected to a server. The portable-type viewer apparatus includes: a selection unit that selects one of the plurality of photography apparatuses; and a photographer ID input unit that inputs a photographer ID that is an ID of a photographer photographing a subject using the selected photography apparatus. The selected photography apparatus further includes a transmission unit that transmits image data of the subject photographed by the selected photography apparatus to the server, and the server includes a recording unit that records the photographer ID and the transmitted image data in association with each other in a case where the photographer ID is input.

30 Claims, 24 Drawing Sheets

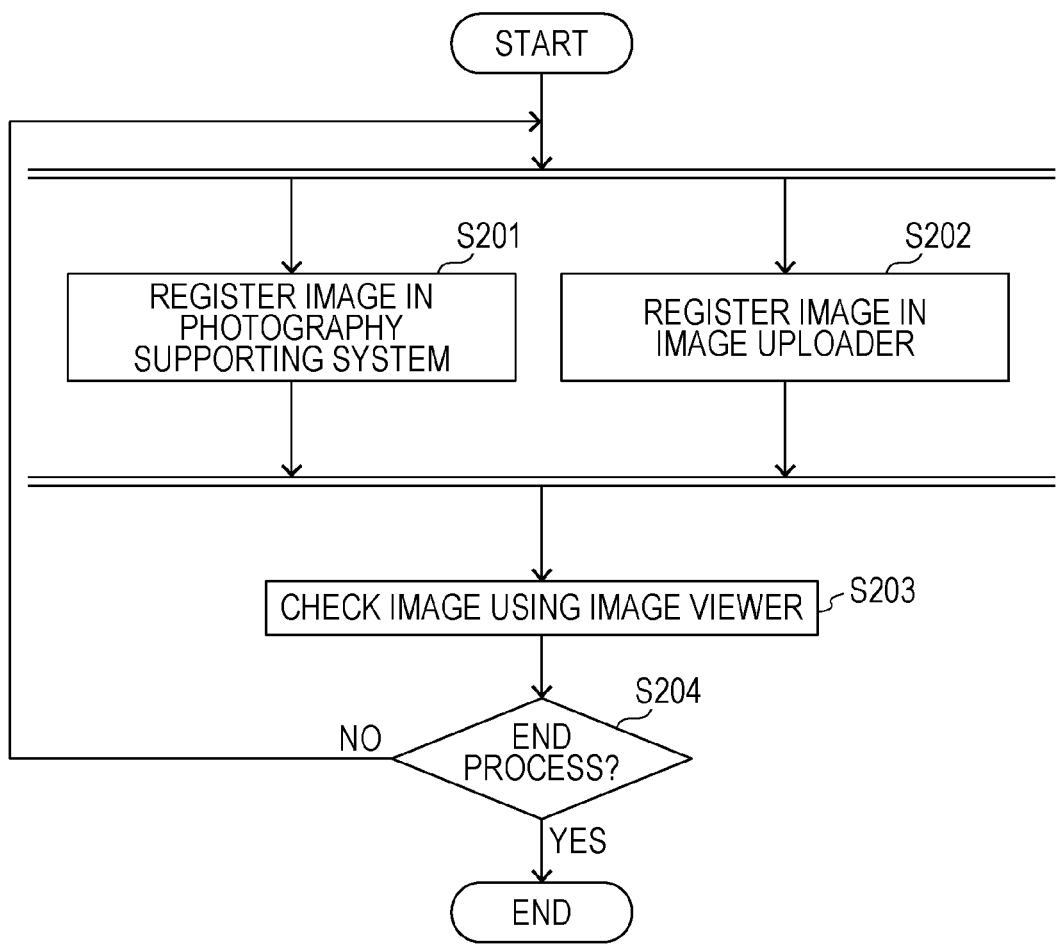

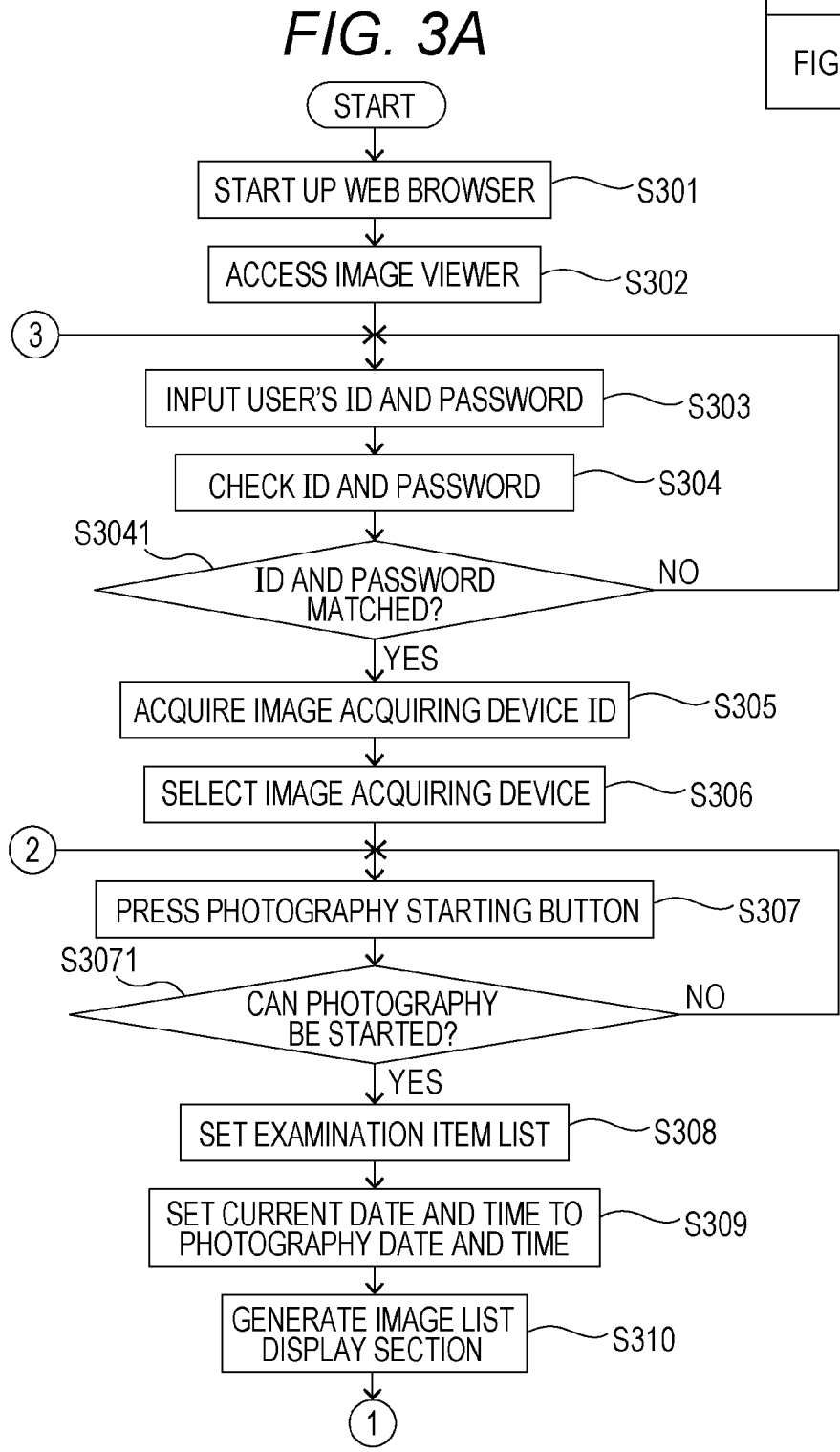

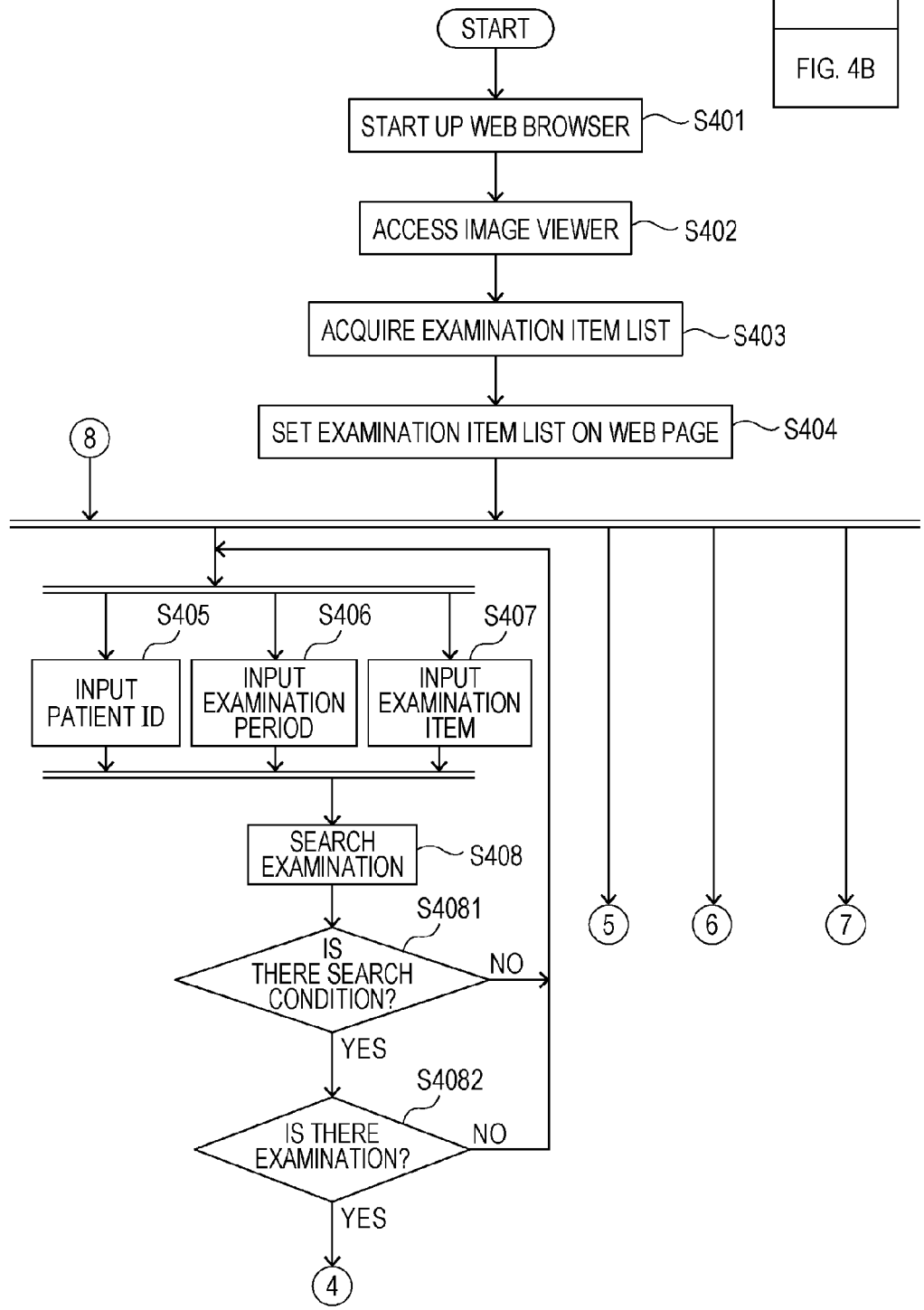

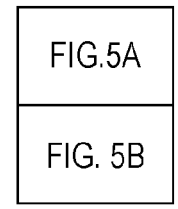
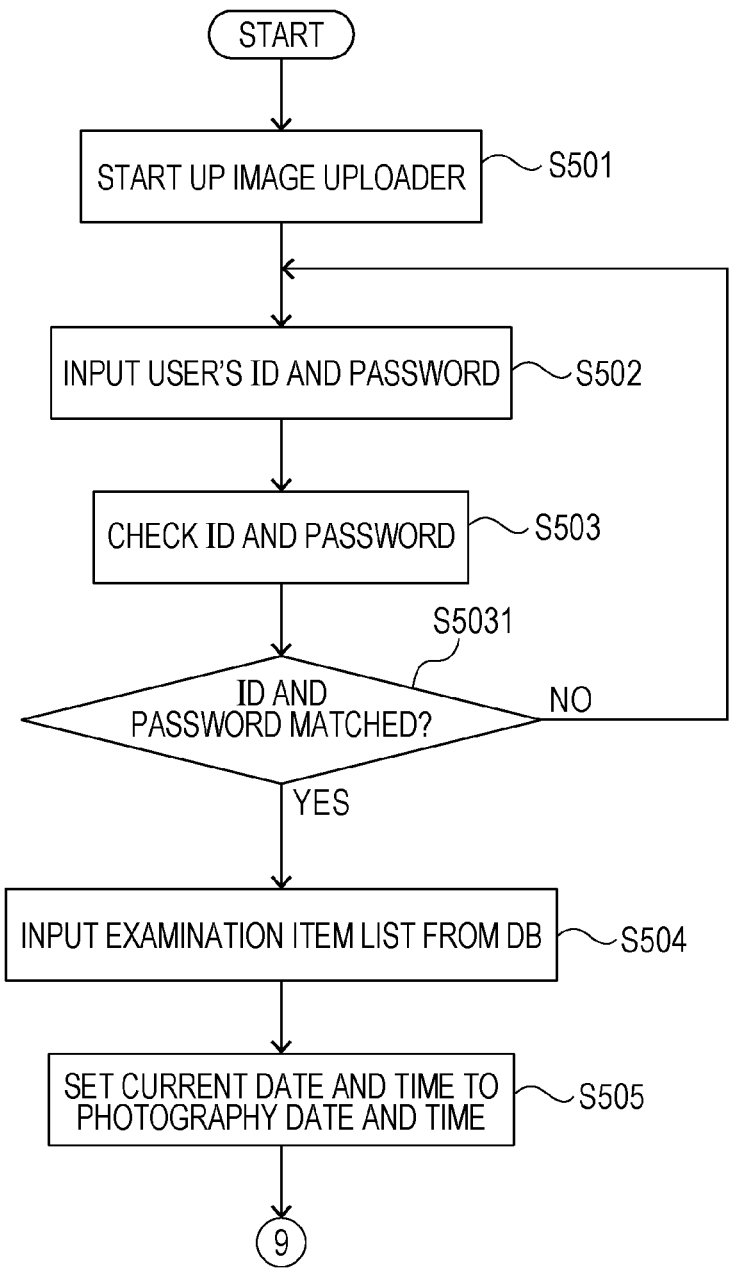
FIG. 5A

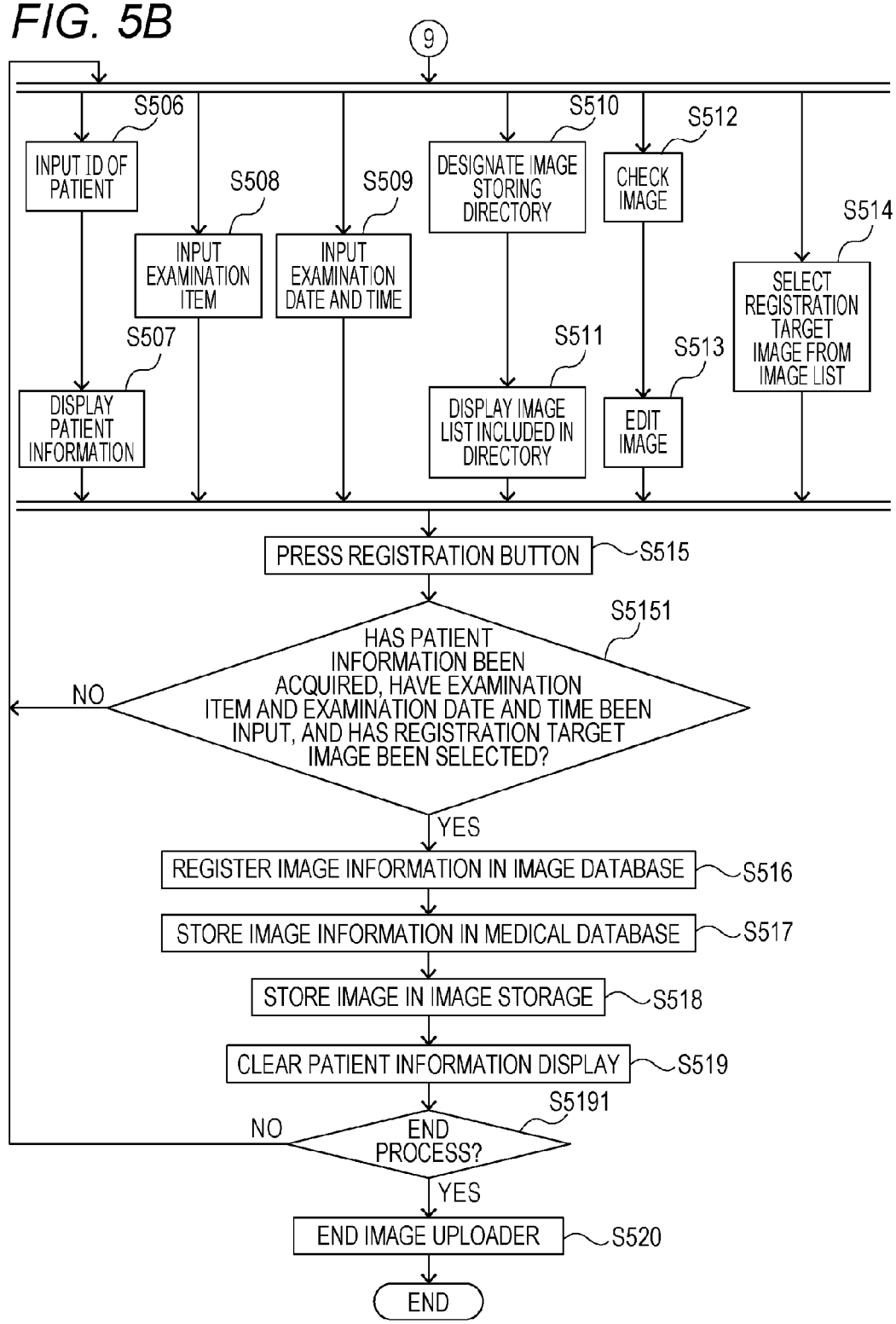

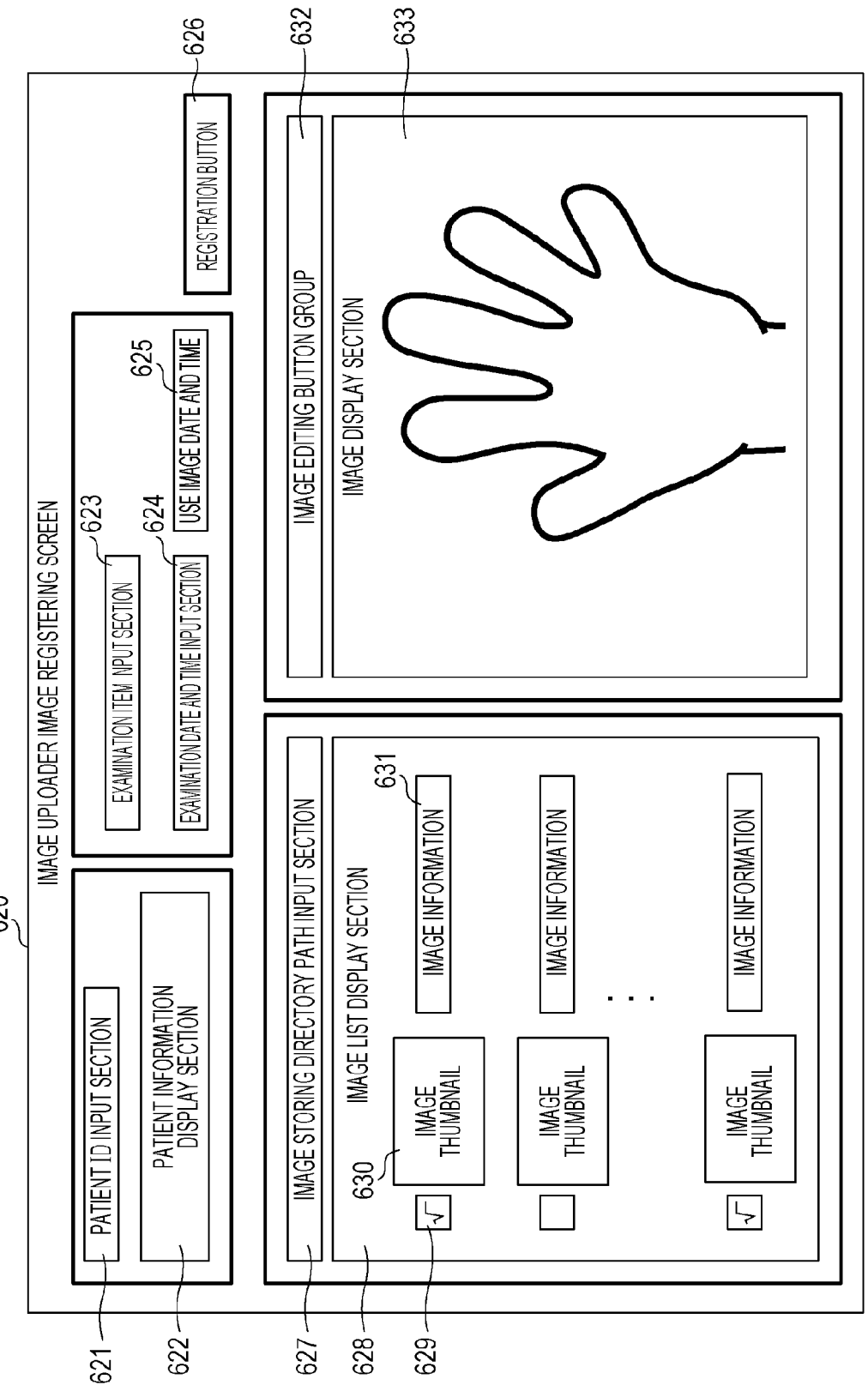

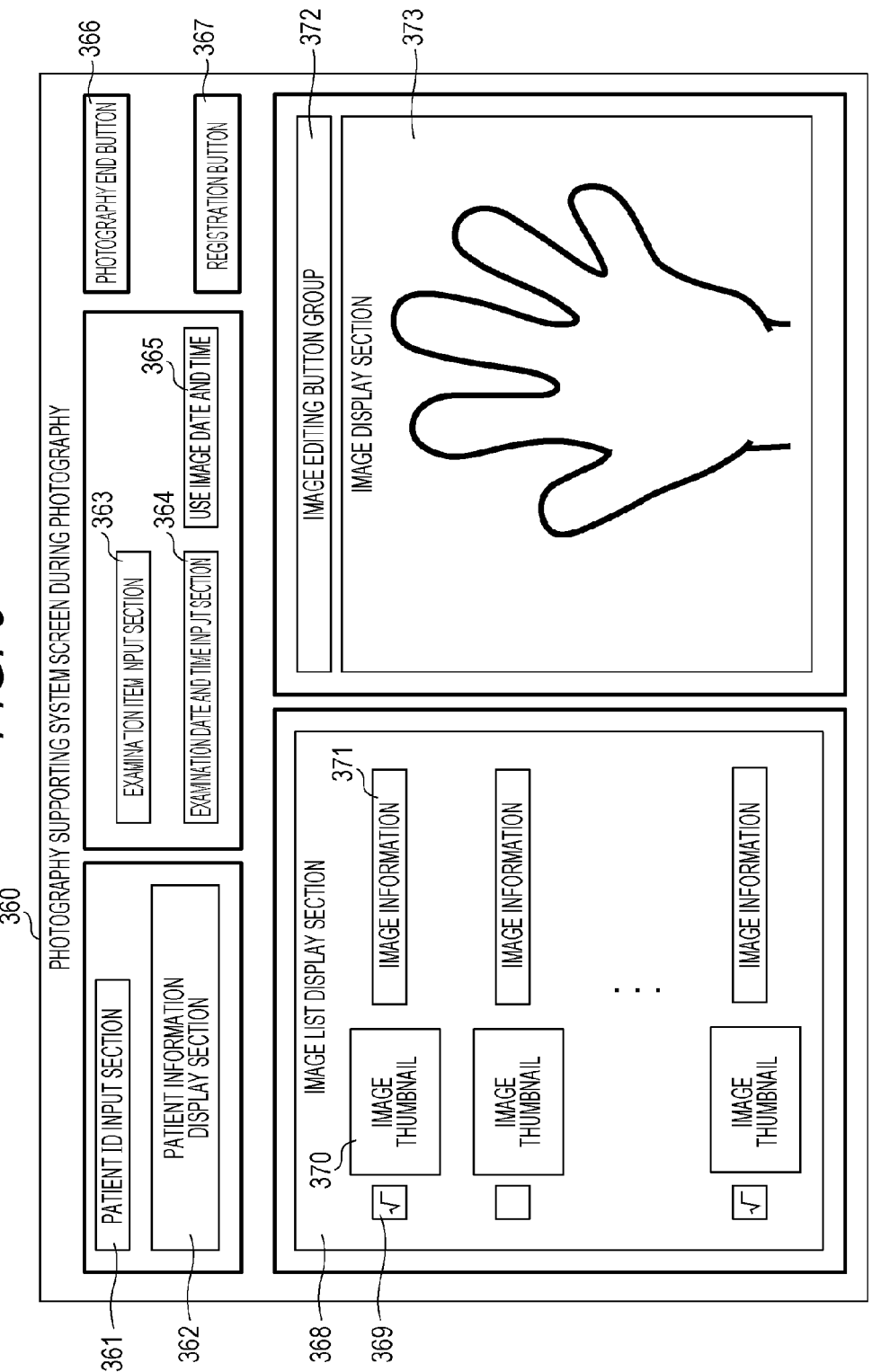

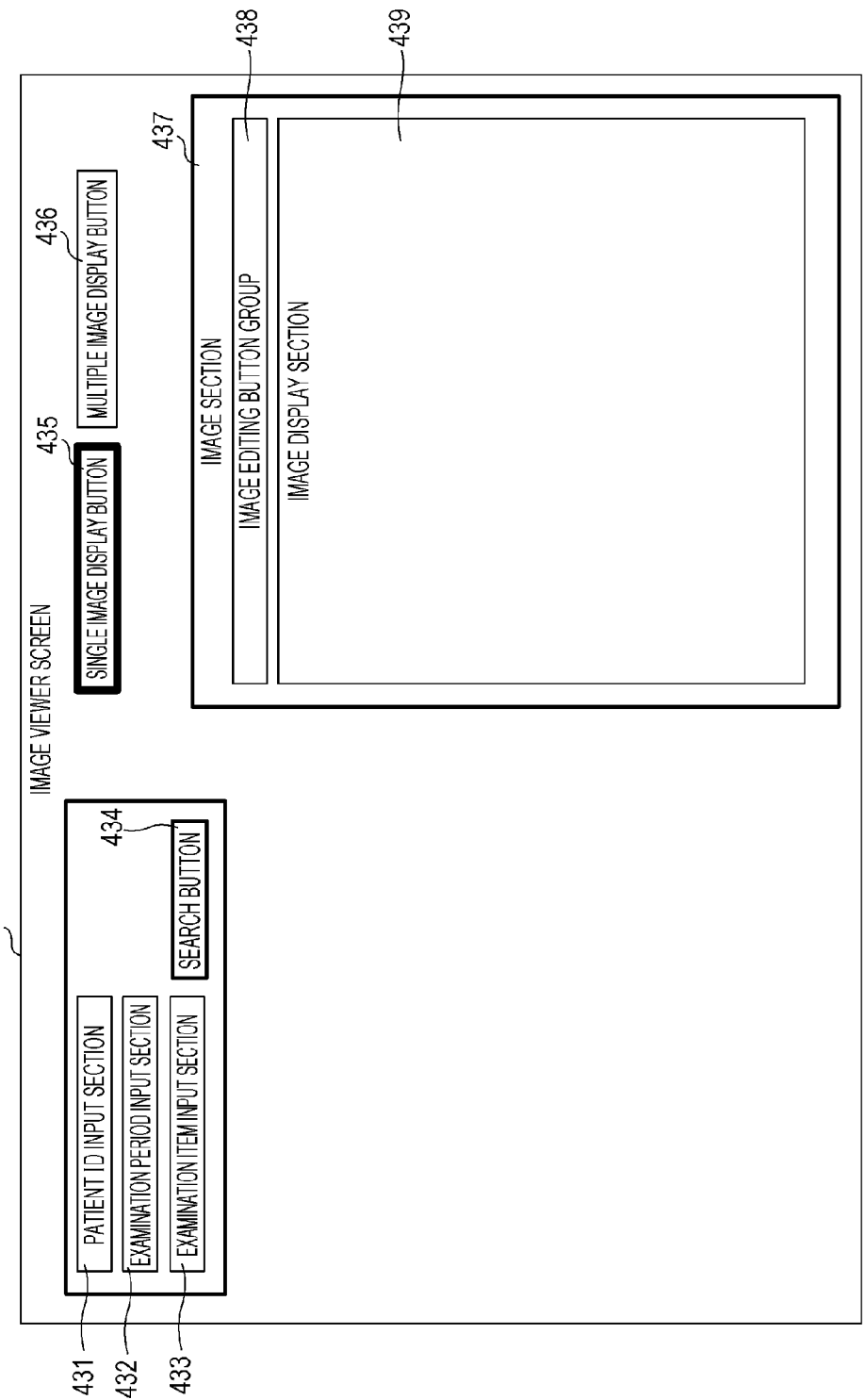

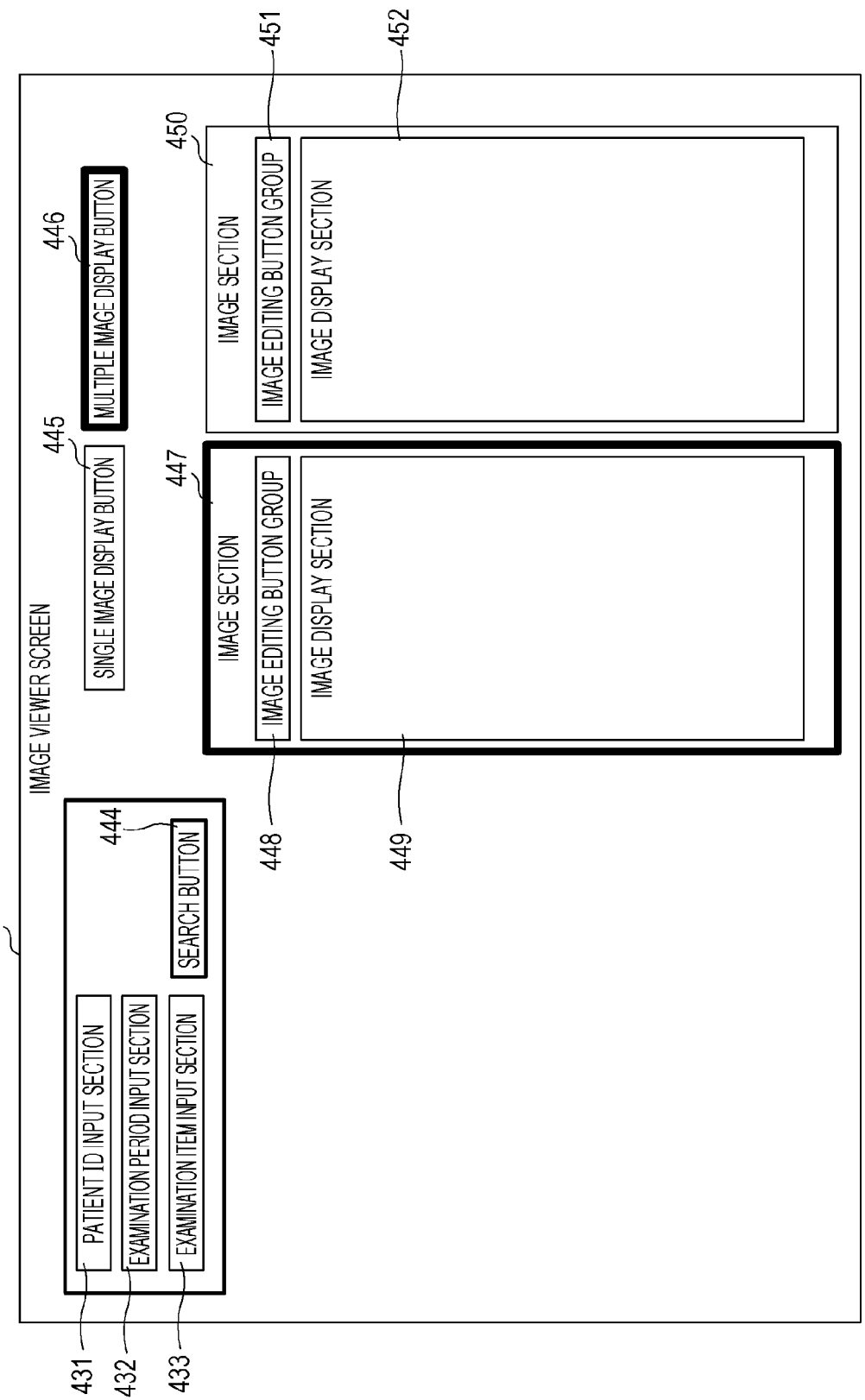

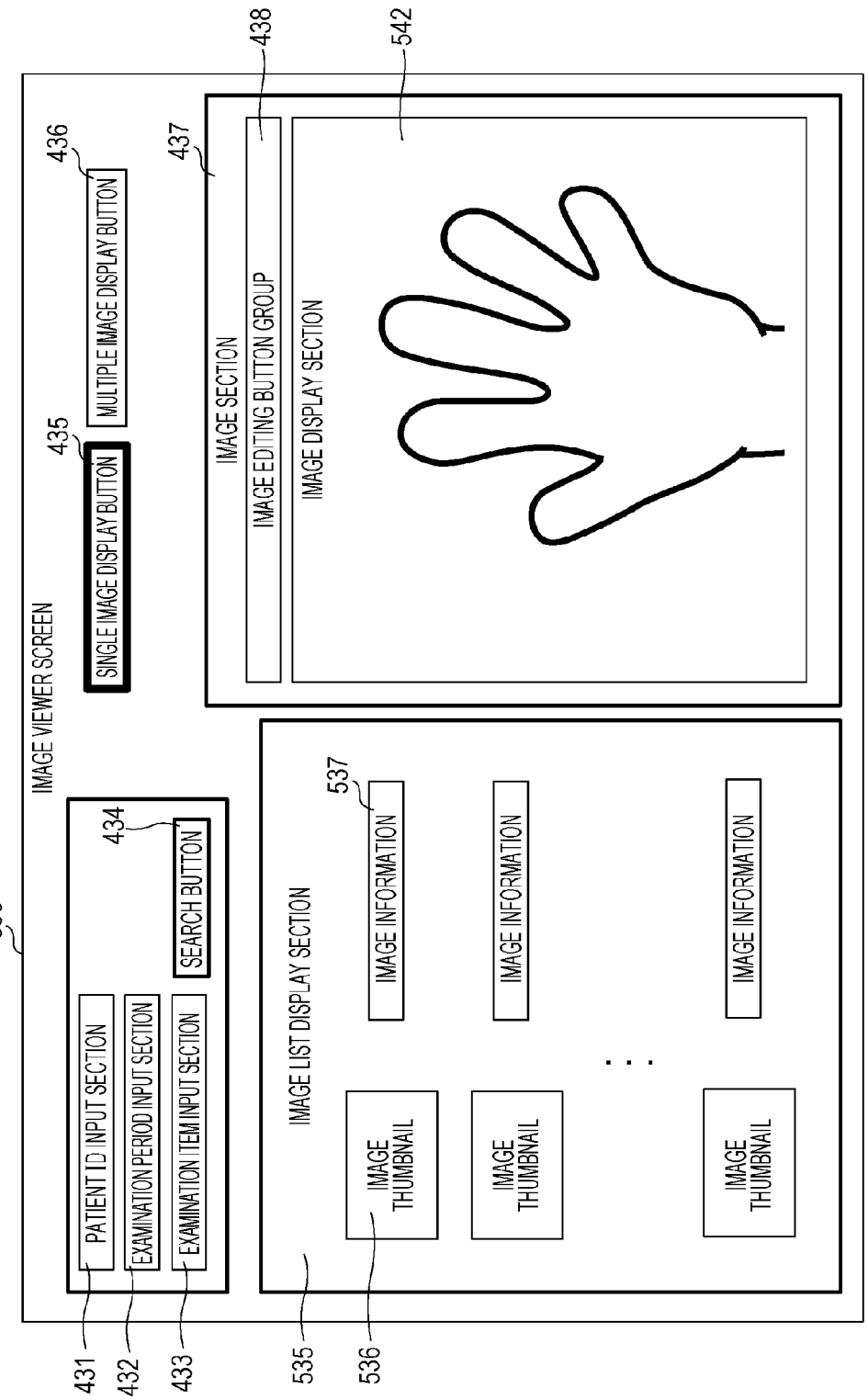

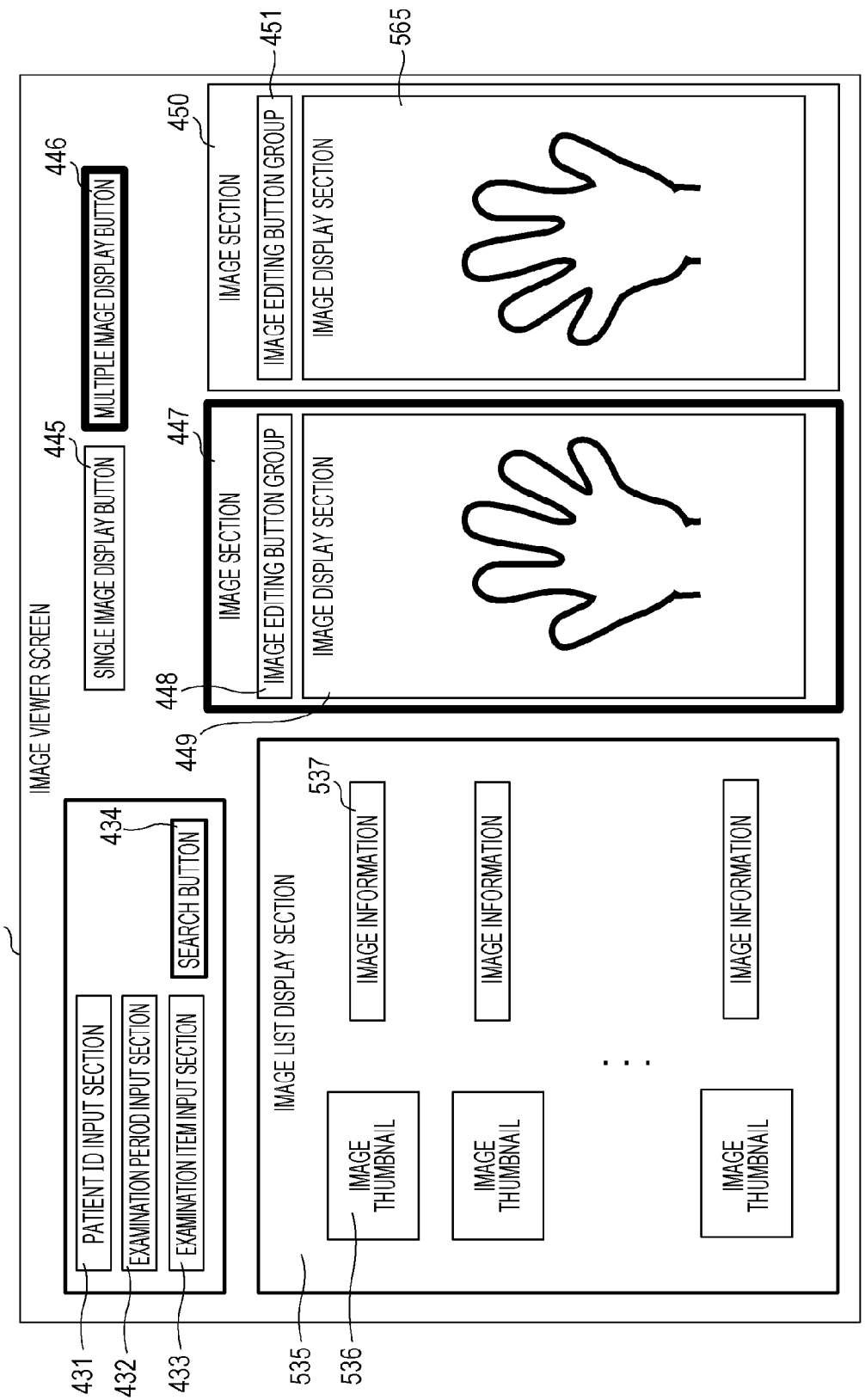

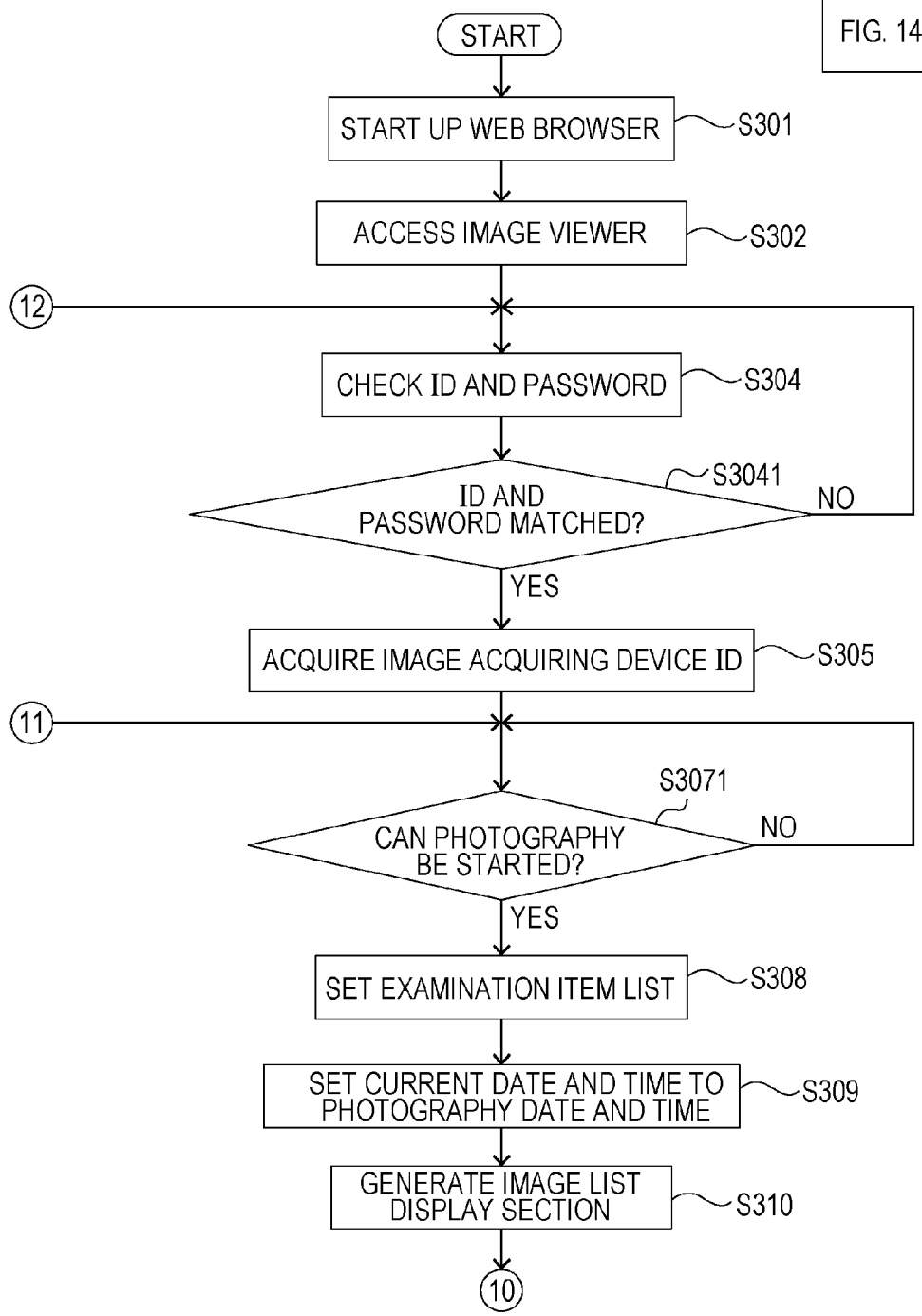

MEDICAL SUPPORT SYSTEM

BACKGROUND OF THE INVENTION

1. Field of the Invention

The present invention relates to a medical support system including a photography supporting system that supports photography.

2. Description of the Related Art

In medical fields, image data acquired by performing photography using a CT apparatus, an MRI apparatus, or the like includes information of photography date, a photographer, a patient, or the like and various kinds of information at the time of performing photography. At this time, the image data is managed by a dedicated server. A user can refer to the image data in a simple manner by searching for the image data based on the information (Japanese Patent Application Laid-Open No. 2004-164320). Here, in medical fields, while there are imaging apparatuses generating image data accompanying information of a patient, a photographer, and the like such as a CT apparatus and an MRI apparatus, there are also imaging apparatuses generating image data without accompanying such information such as a digital camera. In such a case, when some time passes after photography is performed using an imaging apparatus generating image data without accompanying the information, it is not desirable for a user to manually input a large quantity of the image data altogether from viewpoints of the operation efficiency, an input error, and the like.

SUMMARY OF THE INVENTION

An object of the present invention is to provide a medical support system capable of improving the operation efficiency even in a case where a user inputs patient information or the like after photographing a patient.

In addition, the object of the present invention is not limited thereto, and another object thereof may be to achieve an operation and an effect derived by each configuration represented in embodiments of the present invention to be described below, which may not be acquired in accordance with a conventional technology.

A medical support system according to the present invention is medical support system in which a plurality of photography apparatuses and a portable-type viewer apparatus including a display unit are communicably connected to a server, wherein the portable-type viewer apparatus includes: a selection unit that selects one of the plurality of photography apparatuses; and a photographer ID input unit that inputs a photographer ID that is an ID of a photographer photographing a subject using the selected photography apparatus, the selected photography apparatus further includes a transmission unit that transmits image data of the subject photographed by the selected photography apparatus to the server, and the server includes a recording unit that records the photographer ID and the transmitted image data in association with each other in a case where the photographer ID is input.

Further features of the present invention will become apparent from the following description of exemplary embodiments (with reference to the attached drawings).

BRIEF DESCRIPTION OF THE DRAWINGS

FIG. 2 is a flowchart that illustrates the medical support system according to the first embodiment;

FIG. 5 includes FIG. 5A and FIG. 5B which together form a single flowchart that illustrates a case where an image uploader according to a fourth embodiment is used;

FIGS. 8A and 8B are diagrams that illustrate screens of the image uploader according to the fourth embodiment;

FIG. 9 is a diagram that illustrates a screen of the photography supporting system according to the second embodiment during a photography process;

FIGS. 10A and 10B are diagrams that illustrate initial screens of the image viewer according to the third embodiment;

FIGS. 12A and 12B are diagrams that illustrate image data display screens of the image viewer according to the third embodiment;

DESCRIPTION OF THE EMBODIMENTS

Figure 1:
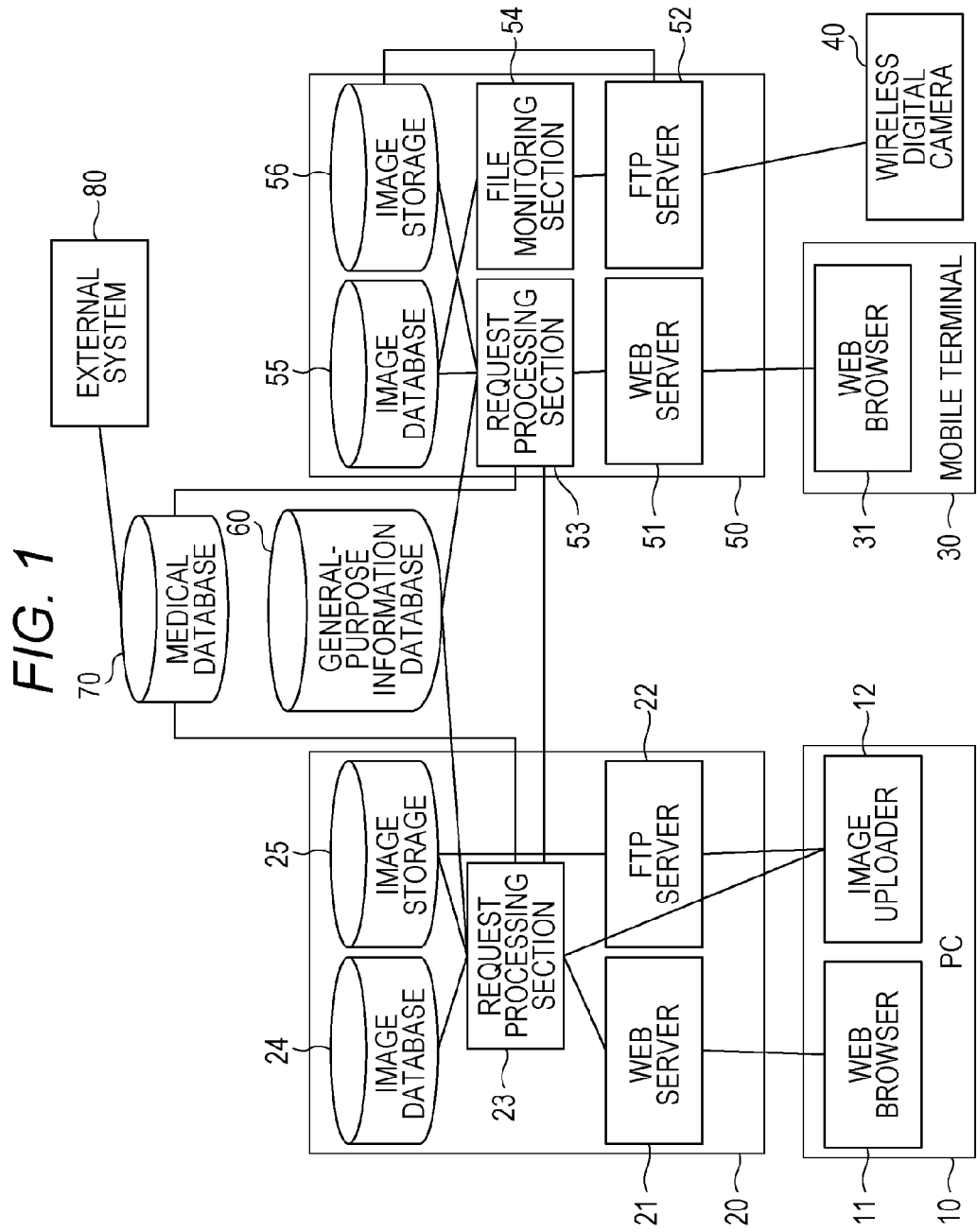
FIG. 1 is a block diagram that illustrates a medical support system according to a first embodiment.

According to an embodiment, there is provided a medical support system in which a plurality of photography apparatuses and a portable-type viewer apparatus including a display unit are communicably connected to a server such as an image management server or a photography supporting server. First, the portable-type viewer apparatus includes: a selection unit that selects one of the plurality of photography apparatuses; and a photographer ID input unit that inputs a photographer ID that is an ID of a photographer photographing a subject using the selected photography apparatus. In addition, the selected photography apparatus further includes a transmission unit that transmits image data of the subject photographed by the selected photography apparatus to the server. Furthermore, the server includes a recording unit that records the photographer ID and the transmitted image data in association with each other in a case where the photographer ID is input.

In addition, according to another embodiment, instead of selecting one of the plurality of photography apparatuses, a photography apparatus ID is configured to be input. In such a case, the photographer ID may not be input. In addition, in a case where a subject is determined to be photographed in which a specific photographer uses a specific photography apparatus, when the photographer ID and the photography apparatus ID are recorded in association with each other, one of the plurality of photography apparatuses does not need to be selected.

According to any one of the embodiments described above, in a case where a photographer ID is input to the portable-type viewer apparatus, the sever may record the photographer ID and the image data transmitted from the selected photography apparatus in association with each other. From this, a user can improved the operation efficiency even in a case where patient information or the like is input together after patients are photographed. In addition, by improving the operation efficiency, an input error can be reduced. At this time, it is preferable that, in a case where the subject is photographed by a photography apparatus other than the selected photography apparatus out of the plurality of photography apparatuses, the recording unit do not record the photographer ID and the image data in association with each other even when the image data of the subject is transmitted to the server.

Here, in medical fields, while there are imaging apparatuses generating image data accompanying information of a patient, a photographer, and the like such as a CT apparatus and an MRI apparatus, there are also imaging apparatuses generating image data without accompanying such information such as a digital camera. In such a case, in a case where the image data does not accompany the information, when the image data is stored in a PC or the like by a photographer, the photographer needs to input the information to an image data storing directory name or a file name through a manual operation while thinking out information memorized by the photographer. However, in medical fields, the user needs to acquire a large quantity of image data without accompanying the information. At this time, when some time passes after photography, it is not desirable for a user to manually input a large quantity of the image data altogether from viewpoints of the operation efficiency, an input error, and the like. Therefore, according to at least one of the above-described embodiments, the operation efficiency, an input error, and the like can be solved.

In addition, it is preferable that the portable-type viewer apparatus further include an information transmitting unit that transmits information including the input photographer ID and the selected photography apparatus to the server. From this, the recording unit can record the photographer ID and the transmitted image data in association with each other after the information transmitting unit transmits the information to the server.

In addition, it is preferable to further include a display control unit that displays an image based on the image data recorded in association with the photographer ID by the recording unit on the display unit in a case where the photographer ID is input by the photographer ID input unit. Furthermore, it is preferable that the portable-type viewer apparatus further include a subject ID input unit that inputs an ID of a subject accompanied with the image data, and, in a case where the ID of a subject is input by the subject ID input unit, the display control unit display data relating to the subject recorded in a CAD server on the display unit through an image management server. In addition, it is preferable that the server further include a recording unit that records data transmitted by the transmission unit and a recording control unit that deletes the data recorded in the recording unit from the recording unit after an elapse of a predetermined period from when photography is performed by the photography apparatus. Furthermore, it is preferable that the portable-type viewer apparatus further include a registration unit that registers the data recorded in the recording unit, and the recording control unit do not delete the data registered by the registration unit after an elapse of a predetermined period.

Here, each embodiment of the present invention will be described with reference to the drawings. Here, each embodiment of the present invention is not limited to wireless communication, and the communication may be performed in a wired manner.

First Embodiment

Medical Support System

First, a medical support system according to a first embodiment will be described with reference to FIG. 1. FIG. 1 is a block diagram that illustrates the medical support system according to the first embodiment. The functional blocks may be configured as one member having the functions thereof. In addition, the functional blocks may be configured by mutually-different servers, while the servers are connected to be communicable with each other.

First, a PC 10, which is an example of an image data processing section, includes a Web browser 11 and an image uploader 12 that are operated by the PC 10. The image uploader 12 adds information to image data that is stored in the PC 10. Then, the image data registered in the image uploader 12 can be read by the Web browser 11 that can communicate with an image management server 20.

The image management server 20 includes a Web server 21 as an example of an image management web generating section and an FTP server 22 as an example of an image management file transmission/reception section. In addition, the image management server 20 includes a request processing section 23, an image database 24, and an image storage 25 that operate on the image management server 20. Furthermore, the request processing section 23 communicates with the Web server 21, the image database 24, and the image storage 25 within the image management server 20. The request processing section 23 operates based on a received command signal. The Web server 21 generates a Web page based on a designated URL, transmits the Web page to the Web browser 11, and communicates with the request processing section 23. The FTP server 22 and the image storage 25 communicate with each other within the image management server 20. The FTP server 22 receives image data from the image uploader 12 and records the image data in the image storage 25. A mobile terminal 30 includes a Web browser 31.

A photography supporting server 50 includes a Web server 51 as an example of a photography supporting web generating section and an FTP server 52 as an example of a photography supporting file transmission/reception section. In addition, the photography supporting server 50 includes a request processing section 53 that operates based on a received command signal, a file monitoring section 54 that performs a predetermined operation when the FTP server 52 receives image data, an image database 55, and an image storage 56. Here, the request processing section 53 communicates with the Web server 51, the image database 55, and the image storage 56 within the photography supporting server 50. The Web server 51 generates a Web page based on a designated URL, transmits the Web page to the Web browser 31, and communicates with the request processing section 53. The FTP server 52 receives image data from a wireless digital camera 40 and records the image data in the image storage 56. The file monitoring section 54 communicates with the FTP server 52 and the image database 55 within the photography supporting server 50. The FTP server 52 and the image storage 56 communicate with each other within the photography supporting server 50. The PC 10 and the image management server 20 are connected to each other on a network in a wired or wireless manner, the Web browser 11 communicates with the Web server 21, and the image uploader communicates with the FTP server 22 and the request processing section 23. In addition, the mobile terminal 30 and the photography supporting server 50 are connected to each other on a network in a wireless manner, and the Web browser 31 and the Web server 51 are connected to be communicable with each other.

The wireless digital camera 40 and the photography supporting server 50 are connected to each other on a network in a wireless manner. In addition, the image management server 20, a general-purpose information database 60, a medical database 70, and the photography supporting server 50 are connected to one another on a network. The general-purpose information database 60 and the medical database 70 communicate with the request processing section 23 and the request processing section 53. In addition, the general-purpose information database 60 stores information of photography items and information of image acquiring devices. The medical database 70 is connected to an external system 80 on a network. In addition, the medical database 70 stores various kinds of information such as information of patients and information of employs relating to medical institutes. The medical database 70 is used for transmission or reception of information to/from an external system.

Photography Supporting System and Image Management System

Here, the "medical support system" according to the first embodiment can be mainly regarded as two systems. First, a first system is a "photography supporting system" that is configured by the mobile terminal 30, the wireless digital camera 40, the photography supporting server 50, and the general-purpose information database 60. At this time, a user can share image data acquired by photography using a photography supporting module at the site in a simple manner. In addition, the other system is an "image management system" that is configured by the PC 10, the image management server 20, the general-purpose information database 60. In this embodiment, although described as two systems, for example, the medical support system may be configured as one server having the functions of the photography supporting server 50 and the image management server 20.

At this time, the image management system mainly has the functions of an "image uploader" and an "image viewer". By the image uploader, image data acquired from a photography apparatus (also referred to as an "image acquiring device") other than the wireless digital camera can be shared. In addition, by using the image viewer, the shared image data can be read at a place at which the PC is installed. The system and the functions will be described below.

Flow of Medical Support System

Here, the flow of the medical support system according to the first embodiment will be described with reference to FIG. 2. FIG. 2 is a flowchart that illustrates the medical support system according to the first embodiment.

First, in Step S201, a user registers image data using the "photography supporting system". In other words, the user registers image data acquired by photography using the wireless digital camera 40 in the image management server 20 by using the mobile terminal 30 and the wireless digital camera 40.

In Step S202, the user registers the image data using the "image uploader" of the "image management system". In other words, the user registers the image data stored in the PC 10 in the image management server 20 using the image uploader 12. The process of Step S202 is performed by the user in a case where a photography target that may not be photographed using the wireless digital camera 40 is photographed using another image acquiring device and the acquired image data is registered or in a case where image data that has been acquired using any method in the past is registered. Here, any one of Steps S201 and S202 may be performed, or both thereof may be performed.

In Step S203, the user checks the image data using the "image viewer" of the "image management system". In other words, the user instructs the PC 10 or the mobile terminal 30 including a Web browser to start the Web browser and checks the image data registered in the image management server 20 using a monitor after accessing the URL of the image viewer. In Step S204, when the operation of checking the image data is determined to be completed, the user ends the Web browser and ends this flow. On the other hand, when the operation is determined not to be completed, the user performs at least one of Steps S201 and S202 again.

Second Embodiment

Photography Supporting System

Figure 3B:
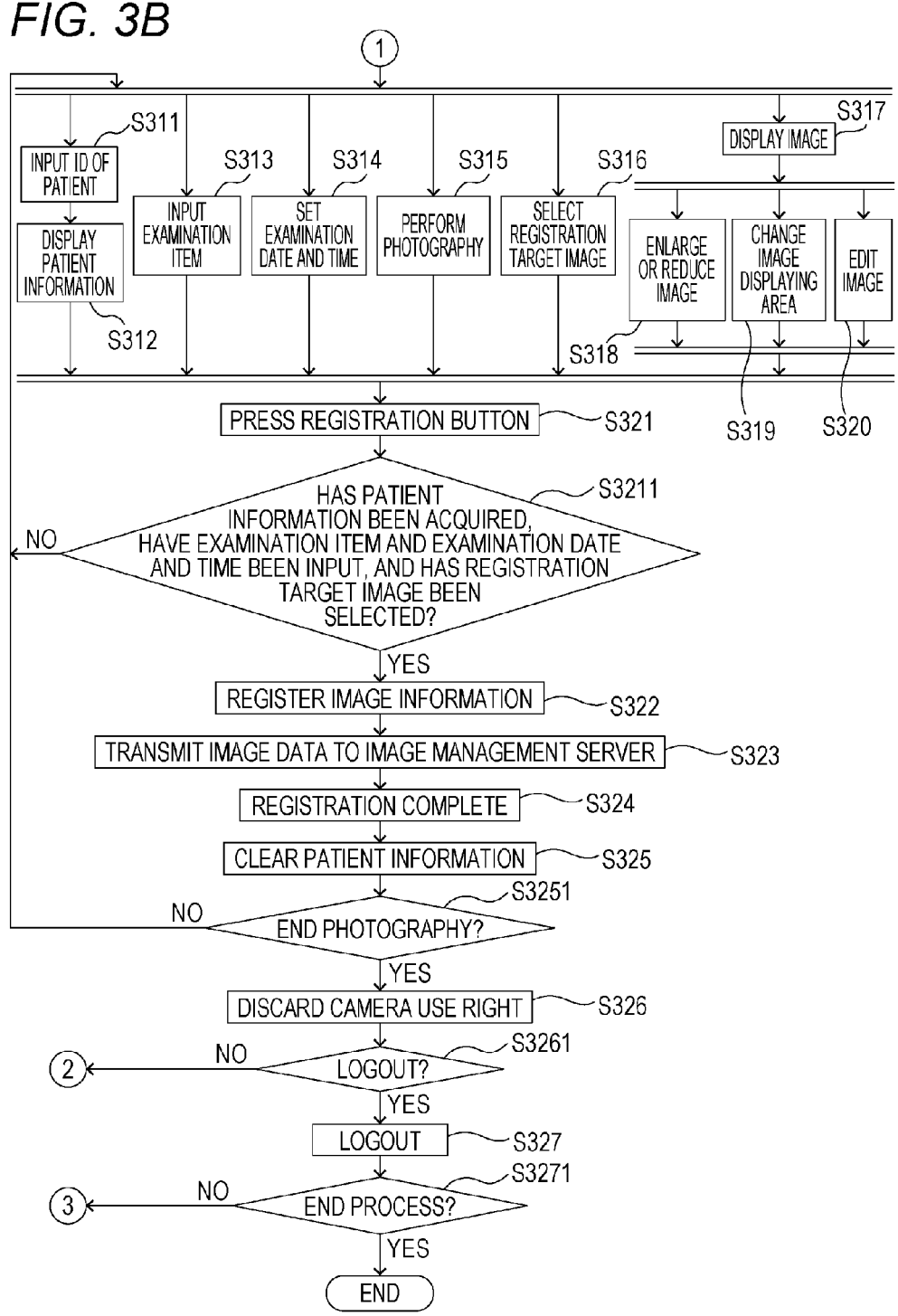
FIG. 3 includes FIG. 3A and FIG. 3B which together form a single flowchart that illustrates a photography supporting system according to a second embodiment.
Figure 7A:
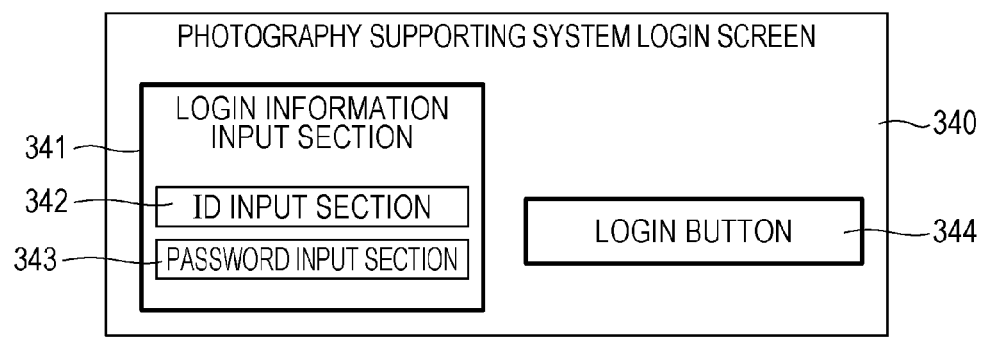
FIGS. 7A and 7B are diagrams that illustrate screens of the photography supporting system according to the second embodiment before photography is performed.
Figure 7B:
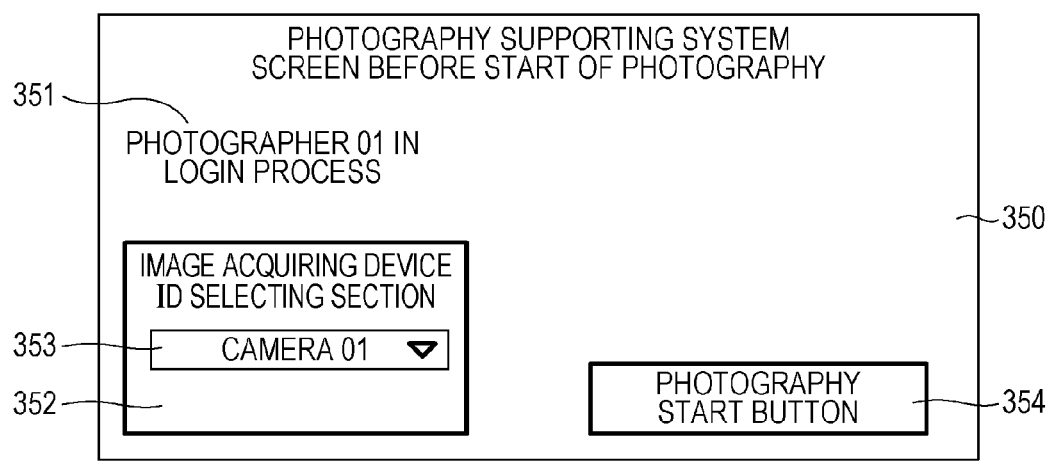
Figure 13:
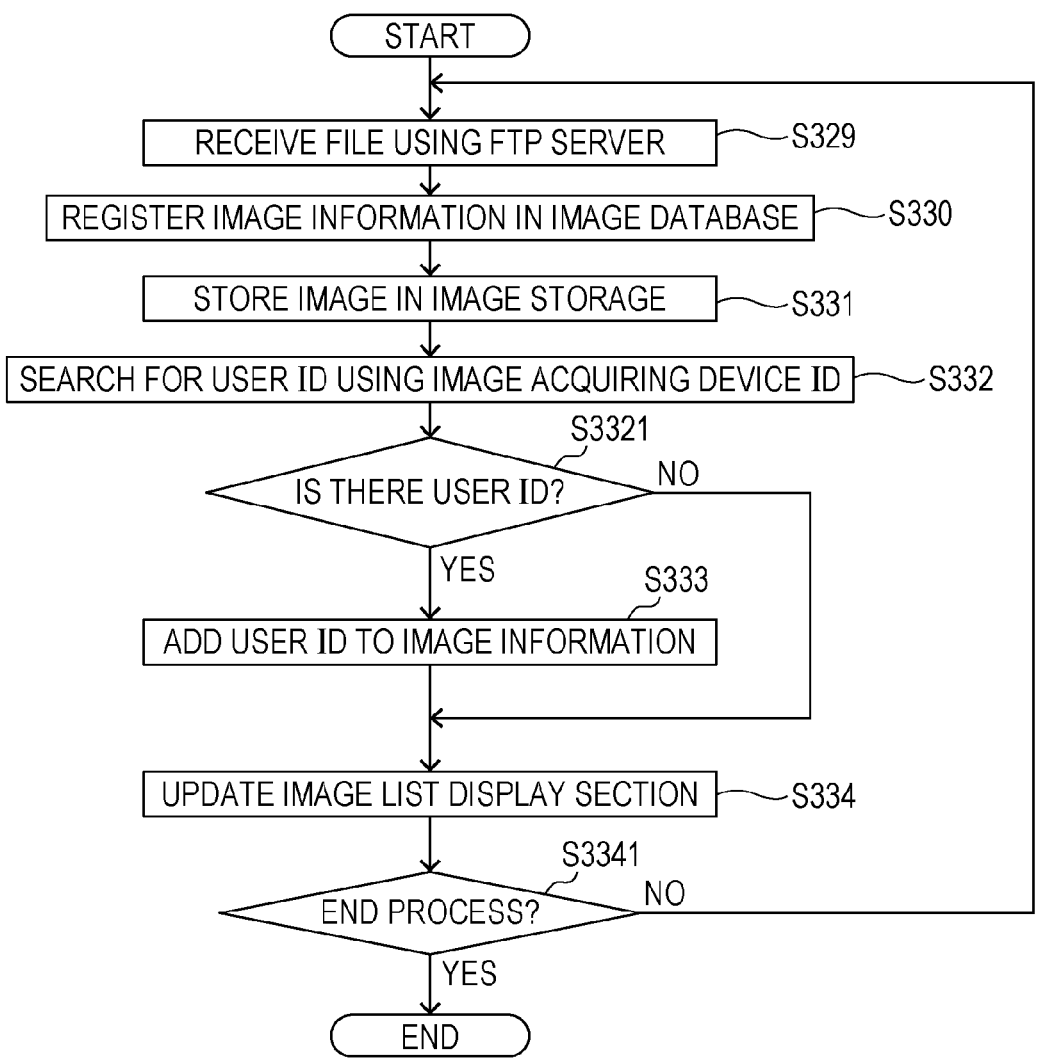
FIG. 13 is a flowchart that illustrates a file monitoring section according to the second embodiment.
Figure 14B:
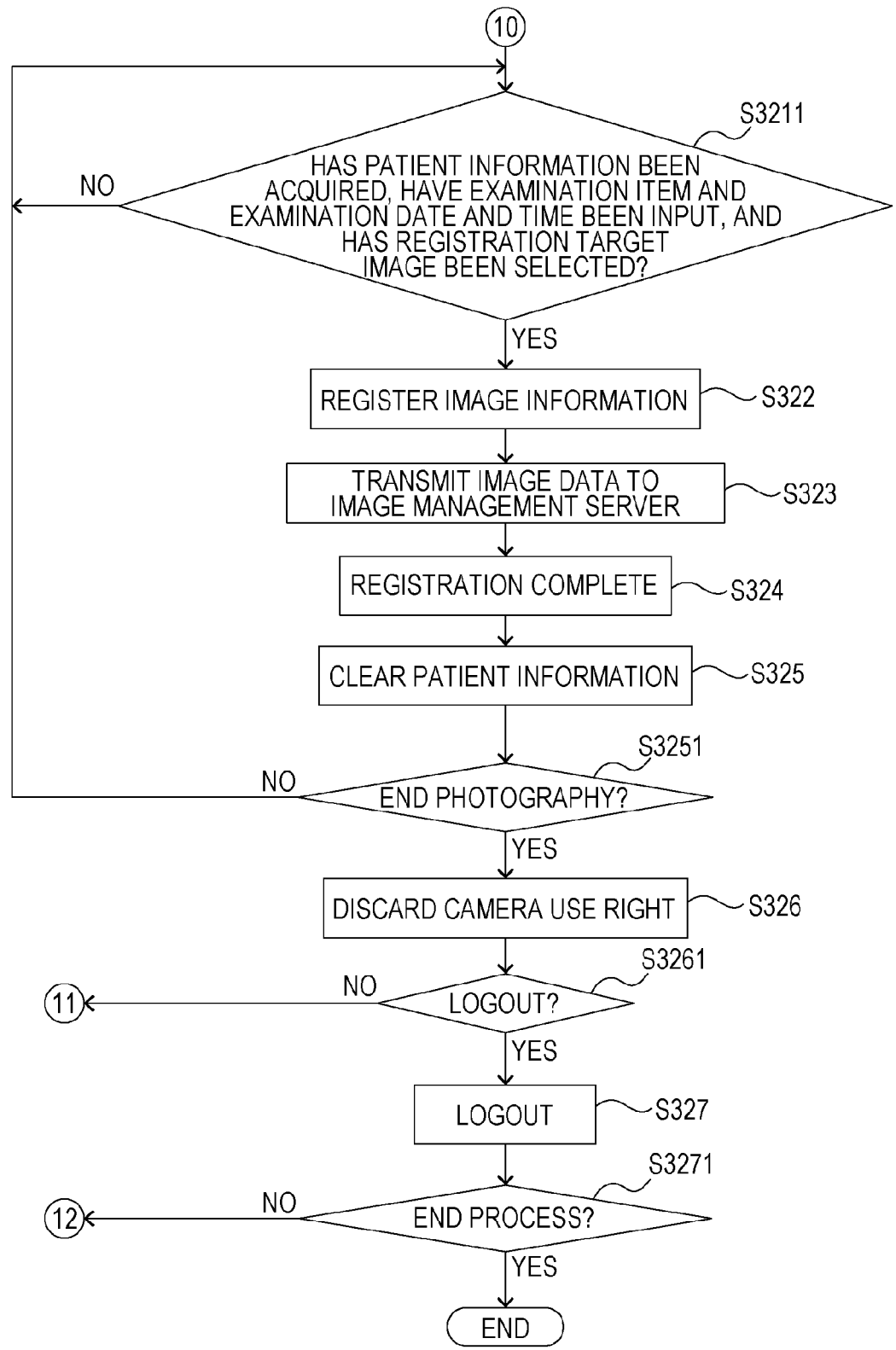
FIG. 14 includes FIG. 14A and FIG. 14B which together form a single flowchart that illustrates the photography supporting system according to the second embodiment in which user operations are not represented.

Next, the flow of a photography supporting system according to a second embodiment will be described with reference to FIGS. 3, 7A, 7B, 9, 13, and 14. FIG. 3 is a flowchart that illustrates the photography supporting system according to this embodiment. FIG. 7A is a diagram that illustrates a login screen of the photography supporting system according to this embodiment, and FIG. 7B is a diagram that illustrates a screen of the photography supporting system according to this embodiment before the start of photography. FIG. 9 is a diagram that illustrates a screen of the photography supporting system according to this embodiment during a photography process. FIG. 13 is a flowchart that illustrates a file monitoring section according to this embodiment. FIG. 14 is a flowchart that illustrates the photography supporting system according to the second embodiment in which user operations are not represented and is a flowchart acquired by excluding steps of user inputs from FIG. 3. In this embodiment, each process of FIG. 14 may be automatically performed at predetermined timing, or at least one process may be performed semi-automatically at the timing when there is a user input.

First, in Step S301, a CPU of the mobile terminal 30 starts up the Web browser 31 in accordance with a user's instruction. In Step S302, the Web browser 31 transmits the URL of a web page 340 of a login screen and a generation request signal to the Web server 51. The Web server 51 generates the Web page 340 of the login screen and transmits the Web page to the Web browser 31 of the mobile terminal 30, and the Web browser 31 of the mobile terminal 30 displays the received Web page 340 of the login screen. In Step S303, the user inputs a user ID to an ID input section 342 of a login information input section 341 of the Web page 340 as the login screen and inputs a password to a password input section 343.

In Step S304, an ID transmission section on the Web page 340 of the login screen transmits the user's ID and password and a login request signal to the Web server 51 of the photography supporting server 50. The Web server 51 transmits the login request signal together with the user's ID and password to the request processing section 53. In addition, the request processing section 53 searches for the received user's ID whether so as to determine whether the received user's ID is present in the medical database 70. Here, in a case where the ID is not present, a login failure signal is transmitted to the Web server 51. On the other hand, in a case where the ID is present, it is checked whether or not a password, which is included in the medical database 70, corresponding to the ID matches the received password. In Step S3041, in a case where the passwords match each other, a login success signal is transmitted to the Web server 51 of the photography supporting server 50. On the other hand, in a case where the passwords do not match each other, a login failure signal is transmitted to the Web server 51 of the photography supporting server 50.

In addition, when the Web server 51 receives the login failure signal, the process is returned to Step S303. On the other hand, when the login success signal is received, the Web server 51 replaces a login button 344 on the Web page 351 of the screen before photography with a logout button and, in Step S305, the Web server 51 transmits an image acquiring device ID list request signal to the request processing section 53. The request processing section 53 acquires an image acquiring device ID group of wireless digital cameras 40 that have been registered in the general-purpose information database 60 from the general-purpose information database 60 and transmits the acquired image acquiring device ID group to the Web server 51 as an image acquiring device ID list. Here, the image acquiring device ID is a unique ID, which is assigned to one image acquiring device such as a wireless digital camera as one, used for identifying a wireless digital camera 40. In addition, the device transmitting the image data may be not the wireless digital camera 40 but, for example, a CT apparatus, an MRI apparatus, an endoscope apparatus, an ophthalmologic apparatus (a hand carry-type fundus camera, an installation-type fundus camera, an OCT, an AO-SLO, an eye refractivity measuring apparatus, a tonometer, or the like), a portable-type X-ray photography apparatus, or the like. The Web server 51 generates a Web page 351 of the screen before the start of photography. In an image acquiring device selecting drop-down list 353, the received image acquiring device ID list is set. In addition, the device transmitting the image data may be any apparatus that can acquire an image used for a medical diagnosis other than the above-described devices.

In Step S306, an image acquiring device used for photography, here, "camera 01" that is the ID of a wireless digital camera 40 is selected from the image acquiring device selecting drop-down list 353 on the Web page 351 of the screen before the start of photography in accordance with a user operation.

In Step S307, when the user presses a photography starting button 354, the Web page 351 before the start of photography transmits the image acquiring device ID, which is selected in Step S306, the user's ID, and a photography start request signal to the Web server 51. Subsequently, in Step S3071, the Web server 51 transmits the image acquiring device ID and the user's ID that have been received, the current data and time in the photography supporting server 50, and a use right acquiring request signal of the image acquiring device to the request processing section 53. The request processing section 53 searches the general-purpose information database 60 for the received image acquiring device ID and tries to register the received user's ID and the received current date and time in association with the image acquiring device ID as registration time. When another user's ID has already been registered, the registered registration time is referred to. In a case where a difference between the registration time and registration time to be registered is an arbitrary time, for example, one hour or more, the user's ID and the registration time that have already been registered are overwritten with the user's ID and the registration time that have been received and transmits a photography start success signal to the Web server 51. On the other hand, in a case where the difference is less than one hour, the request processing section 53 transmits a photography start failure signal to the Web server 51. The process of acquiring the use right of an image acquiring device in Step S3071 is a function for preventing that another user's ID, which is in use, is overwritten by the image acquiring device stored in the general-purpose information database 60. When the overwriting is performed, the image data acquired by photography using a target image acquiring device is registered in association with the user's ID transmitted in Step S307 in the subsequent process.

In addition, in a case where the photography start failure signal is received by the Web server 51, the process is returned to Step S307. On the other hand, in a case where the photography start success signal is received by the Web server 51, in Step S308, the Web server 51 transmits an examination item list request signal to the request processing section 53. The request processing section 53 acquires an examination item group that has been registered in the general-purpose information database 60 from the general-purpose information database 60 and transmits the examination item group to the Web server 51 as an examination item list. The Web server 51 generates a Web page 360 of the screen during photography, sets the received examination item list in an examination item input section 363, and forms a state in which the user can select an examination item included in the examination item list. Here, the examination item, for example, is a keyword representing the type of examination or the type of image data such as a photograph during an operation, a pathology photograph, an echographic examination image, or an X-ray photograph.

In Step S309, the Web server 51 acquires the current date and time of the photography supporting server 50 and sets the date and time in an examination date and time input section 364 on the Web page 360 of the screen during photography.

In Step S310, the Web server 51 transmits an image information acquisition condition and a photographed image request signal to the request processing section 53. Here, the image information acquisition condition is a condition for selecting image information that is based on an image list item displayed on the image list display section 368 of the screen during photography from the image database. For example, "50 records of image information in order being photographed recently", "image information of image data photographed from three days ago until today", "image information of an user ID of user 01", "image information of an image acquiring device ID of camera 01", "all image information", or the like. There may be a plurality of the image information acquisition condition. As the image information acquisition condition, a condition that is set in advance in the Web server 51 is used. Alternatively, a user interface for changing the image information acquisition condition may be arranged on the Web page 360 of the screen during photography. In such a case, when the image information acquisition condition changes in the user interface, the process is returned to the start of Step S310. Here, the image information is information of image data such as an image information ID used for identifying image information, the name and the file size of the photographed image data, a file path in an image storage, an URL used for displaying image data, an image acquiring device ID, the number of pixels in a horizontal width, the number of pixels in the height, generation date and time, photography date and time, update date and time, image rotation information, and an image acquiring device ID. The request processing section 53 acquires an image information group from the image database based on the received photographed image acquisition condition and transmits the acquired image information group to the Web server 51. The Web server 51 adds a set of a thumbnail image corresponding to image information and image information to the image list item of the image list display section 368 of the Web page 360 of the screen during photography. However, in a case where a flag indicating the completion of deletion is added to image information, the image list item is not added. In addition, a check box 369 is attached to each image list item, and, by operating the check box 369, the selection of registration target image data is performed in Step S316. The Web server 51 transmits the Web page 360 of the screen during photography to the Web browser 31, and the Web browser 31 displays the Web page 360 of the received screen during photography.

In Step S311, the ID of a patient is input to a patient ID input section 361 in accordance with a user's instruction. In Step S312, the Web page 360 of the Web page 360 during photography checks that the ID of the patient input to the patient ID input section 361 satisfies the character string rule of a patient's ID and transmits the received ID of the patient and a patient information acquiring request signal to the request processing section through the Web server 51. The request processing section 53 searches for the received ID of the patient so as to determine whether the received ID of the patient is present in the medical database 70. In a case where the received ID of the patient is not present therein, the request processing section 53 transmits a patient ID search failure signal to the Web server 51. On the other hand, in a case where the received ID of the patient is present therein, the request processing section 53 transmits patient information, which is included in the medical database 70, corresponding to the ID of the patient to the Web server 51. The patient information, for example, is information relating to a patient such as the name and the ID of a patient, the gender of a patient, date of birth of a patient, and the age of a patient. When the patient ID search failure signal is received by the Web server 51, the Web server 51 displays an indication of the patient ID search failure on the Web page 360 of the screen during photography and does not display the patient information in the patient information display section 362. On the other hand, when the patient information is received by the Web server 51, the Web server 51 displays the patient information on the patient information display section 362 of the Web page 360 of the screen during photography.

In Step S313, the user selects an examination item by operating the examination item input section 363 of the Web page 360 of the screen during photography. In Step S314, the user inputs examination date and time by operating the examination date and time input section 364 of the Web page 360 of the screen during photography. However, in a case where one or more pieces of the registration target image data including date and time information are included in the registration target image data group selected in Step S316, the user may select to employ the oldest date and time information of date and time information as examination date and time. In such a case, the user operates a toggle button 365 used for using date and time included in the registration target image data group to be turned on. In Step S315, when the user performing photography using the wireless digital camera 40 having the image acquiring device ID selected in Step S306, the wireless digital camera 40 transmits the image data generated by the photography to the FTP server 52. A unit that receives the image data may not use an FTP server. For example, there is a Web server using HTTP communication or a DICOM server using an image communication protocol.

Here, in Step S329 illustrated in FIG. 13, when the FTP server 52 receives the image data, in Step S330, the file monitoring section 54 acquires a thumbnail image and image information by analyzing the received image data. In addition, the received date and time are added to the image information as transmission date and time. While a wireless digital camera 40 from which the image data has been transmitted may be identified based on the image acquiring device ID included in the image information, as another identification method, for example, there is a method or the like in which the transmission destination directory of the image data of the wireless digital cameras is divided to be dedicatedly used for each wireless digital camera 40. In such a case, the path of a transmission destination directory and an image acquiring device ID are registered in the general-purpose information database 60 in advance with being associated with each other, and, when the image data is received, the general-purpose information database 60 is referred to using the directory path as a key, an image acquiring device ID corresponding to the image data can be checked, and the image acquiring device ID may be added to the image information. The thumbnail image is a reduced image of the received image data. In addition, the thumbnail image is a rotated thumbnail image on which image rotation information included in the image information is reflected. The file monitoring section 54 registers the acquired image information in the image database 55 and transmits a new image input signal to the Web server 51. In Step S331, the file monitoring section 54 stores the image data received by the FTP server 52 in Step S329 and the thumbnail image acquired in Step S330 in the image storage 56. In Step S332, the file monitoring section 54 searches the general-purpose information database 60 by using the image acquiring device ID included in the image information acquired in Step S330 as a key, and, in a case where a user's ID corresponding to the image acquiring device ID can be acquired in Step S3321, the user's ID is additionally registered in the image information of the image database 55 in Step S333. On the other hand, in a case where the user's ID may not be acquired, any additional operation is not performed. In addition, while the operation of the file monitoring section 54 described above is continued while the power of the server is turned on, it may be determined whether the power is turned off in Step S3341. At this time, in a case where the power of the server is determined to have been turned off, the flow of the file monitoring section ends. Subsequently, in Step S334, the Web server 51 performs the same process as that of Step S310. In Step S316, the user may select registration target image data by operating a check box 369 attached to an arbitrary image list item of the image list display section 368.

In Step S317, the user selects an arbitrary image list item from the image list item group displayed on the image list display section 368 by operating a pointing device such as a mouse connected to the PC, and, by referring to the URL used for displaying image data from the image information corresponding to the selected image list item, the image data may be displayed on the image display section 373. In addition, in a case where image processing information or image additional information is included in the image information, the image data on which such information is reflected is displayed. The image processing information and the image additional information are generated in Step S320.

In Step S318, the user may enlarge or reduce the image data displayed on the image display section 373 by performing a specific operation. As a method for performing the operation, for example, a pinch-in/pinch-out operation or a key operation of the mobile terminal 30 may be employed.

In Step S319, the user may move a display area of the image data displayed on the image display section 373 by performing a specific operation. As a method for performing the operation, a swiping operation or a key operation of the mobile terminal 30 may be employed.

In addition, in Step S320, the user may add the image processing information or the image additional information to the image information by performing an editing operation of the image data that is displayed on the image display section 373 by pressing an arbitrary image editing button included in the image editing button group 372. When the editing operation is performed, a result of the editing operation is displayed on the image display section. Here, the editing operation is an operation of generating image processing information by rotating an image, performing vertical reversal/horizontal reversal of an image, selecting and trimming an arbitrary rectangular area in an image, adjusting colors, directly writing a graphic or a text in the image data or an operation of generating the image additional information by adding a comment to the image data or adding information used for displaying a graphic or a text to be superimposed on the image. In addition, the Web page 360 of the screen during photography registers the image information updated by the editing operation in the image database 55 through the Web server 51.

In Step S321, when the user presses a registration button 367, an image registering process is started. In Step S3211, the Web page 360 of the screen during photography determines whether valid patient information has been acquired in Step S312, an examination item has been selected in Step S313, the examination date and time has been input in Step S314, and one or more pieces of registration target image data have been selected in Step S316. In addition, in a case where the toggle button 365 used for using date and time included in the image data is turned on in Step S314, the Web page 360 of the screen during photography selects image data having the oldest date and time information from among the registration target image data selected in Step S316 and employs the date and time as examination date and time. In such a case, the examination date and time are assumed to have been input. In a case where there is no image data having date and time information, the image uploader 12 presents a message indicating that there is no image data having date and time information to the user, and the process is returned to Step S310.

In Step S322, the Web page 360 of the screen during photography transmits an image information group of the registration target image data group and an image information registering request signal to the Web server 51 through the request processing section 53. The request processing section 53 registers the received registration target image information group in the image database 24. In addition, the request processing section 23 additionally registers image information of copies of the each registration target image data and each thumbnail image transmitted in Step S323 in the image management server 20 in the corresponding registration image data information. Here, the image information of the image management server 20, for example, is information relating to the image data such as a file path of the registration target image data in the image storage 56 and an URL used for displaying the image data. In addition, the request processing section 23 additionally registers a unique examination ID that is the same for all the registered registration target image information group. Furthermore, the request processing section 23 registers the management image information also in the medical database 70. The image information registered in the medical database 70 may be used by an external system 80. For example, an electronic clinical record system that is an external system may associate the URL registered in the image management server 20 with the user interface. Then, the user can refer to an image corresponding to a click position by clicking on the user interface.

In Step S323, the request processing section 53 generates copies of the image data and the thumbnail mage corresponding to the received registration target image data group from the image data group and the thumbnail image group stored in the image storage 56 and transmits the generated copies of the image data and the thumbnail image to the FTP server 22. The FTP server 22 registers the received copies of the image data and the thumbnail image in the image storage 56. In Step S324, the request processing section 53 additionally registers an image management system registration completion flag in the image information corresponding to the registration target image data registered in the image database 55. The request processing section 53 transmits a registration completion signal to the Web server 51, and the Web server 51 that has received the registration completion signal displays a message indicating the completion of registration in the Web page 360 of the screen during photography. In addition, in Step S325, the Web page 360 of the screen during photography blanks the ID of the patient input to the patient ID input section and blanks the patient information display section 362.

In Step S3251, in a case where the user ends photography, when the user presses a photography end button 366 on the Web page 360 of the screen during photography, in Step S326, the Web page 360 of the screen during photography transmits the image acquiring device ID and a photography end signal to the request processing section 53 through the Web server 51. The request processing section deletes the user's ID corresponding to the image acquiring device ID of the general-purpose information database 60, and the Web browser 31 transits to the Web page 351 of the screen before photography. On the other hand, in a case where the user does not end photography, the process is returned to Step S310.

In Step S3261, in a case where the user logs out from the photography supporting system, when the user presses a logout button on the Web page 351 of the screen before photography, in Step S327, the Web page 351 of the screen before photography clears a login information input section and replaces the logout button with the login button. In Step S3271, in a case where the photography supporting system is not completed in that state, the process is returned to Step S303. In a case where the user does not logout from the photography supporting system, the process is returned to Step S307.

Third Embodiment

Image Viewer

Figure 4B:
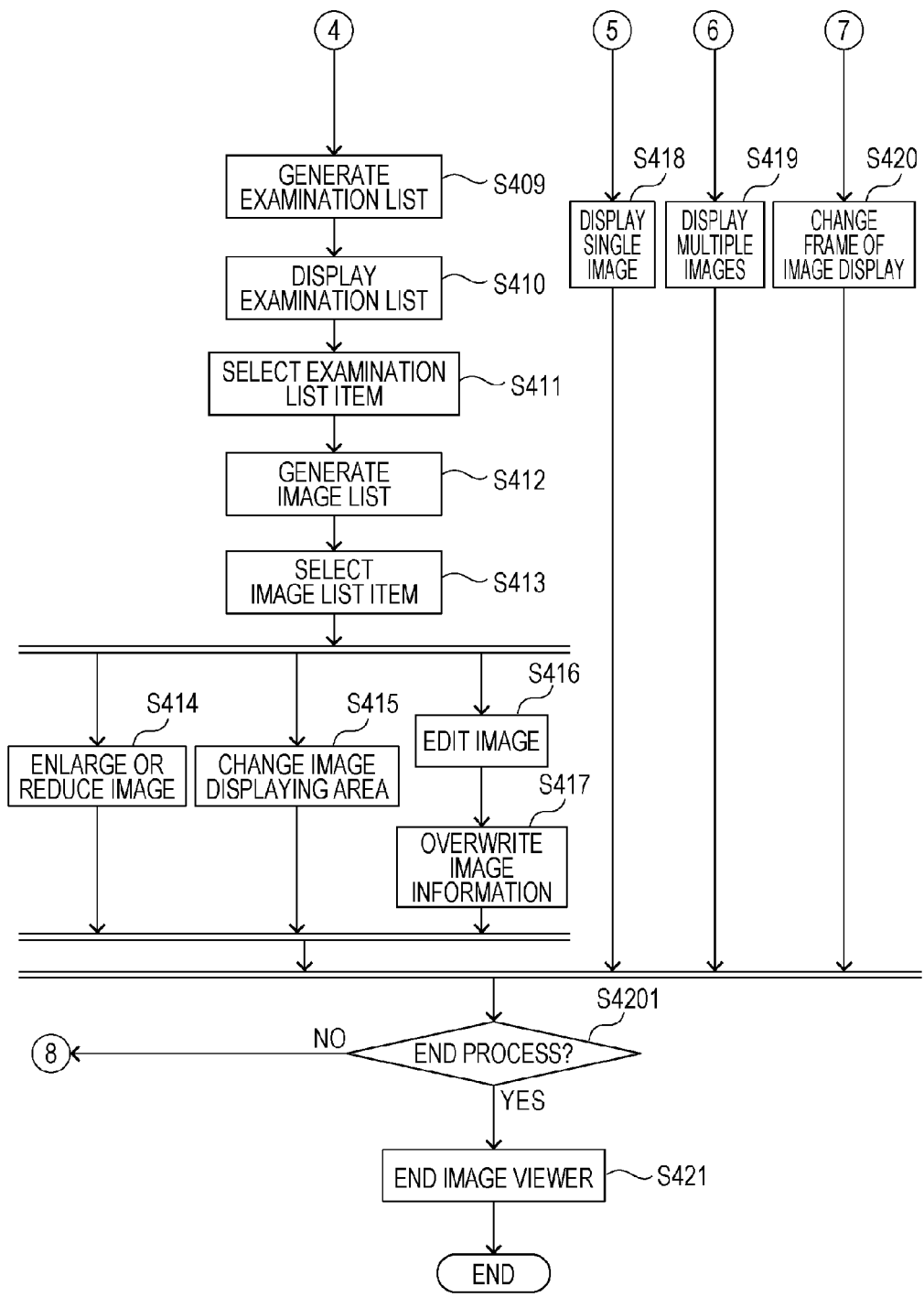
FIG. 4 includes FIG. 4A and FIG. 4B which together form a single flowchart that illustrates a case where an image viewer according to a third embodiment is used.
Figure 11A:
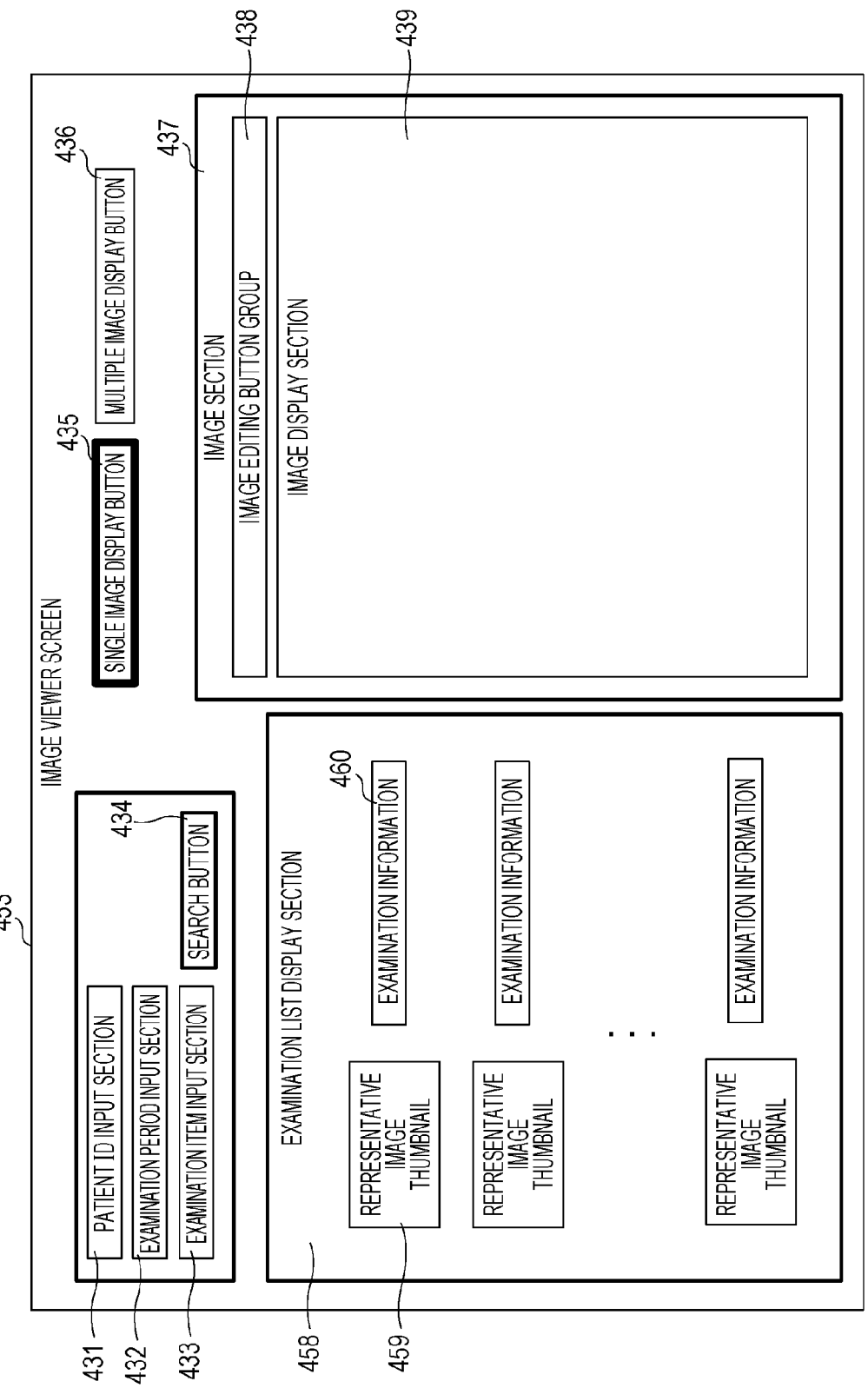
FIGS. 11A and 11B are diagrams that illustrate search result screens of the image viewer according to the third embodiment.
Figure 11B:
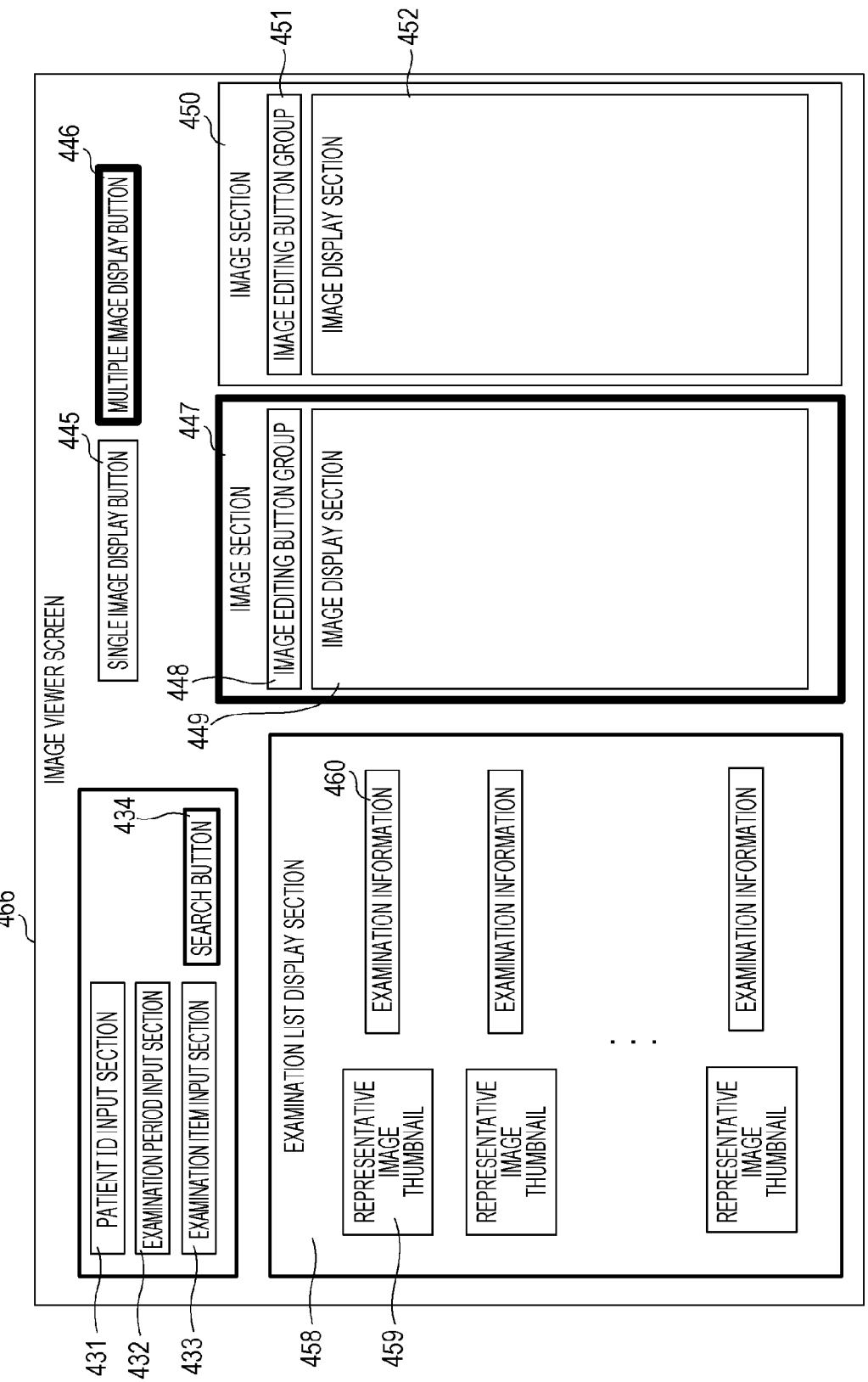
Figure 15:
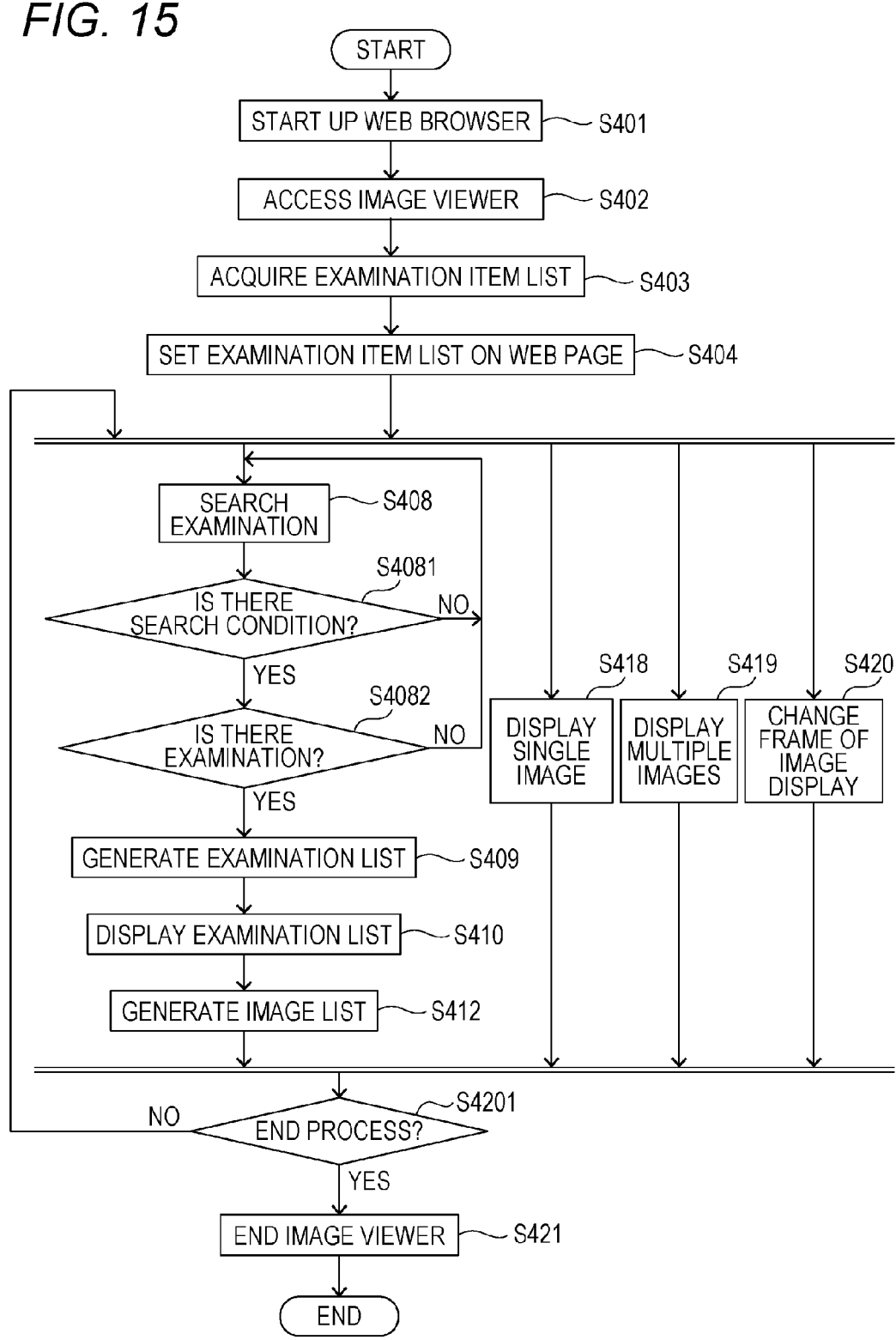
FIG. 15 is a flowchart in a case where the image viewer according to the third embodiment is used in which user operations are not represented.

The flow in a case where an image viewer according to a third embodiment is used will be described with reference to FIGS. 4, 10, 11, 12, and 15. FIG. 4 is a flowchart in a case where the image viewer according to this embodiment is used. FIG. 10A is a diagram that illustrates an initial screen 430 in a state in which a single image is displayed in the image viewer according to this embodiment, and FIG. 10B is a diagram that illustrates an initial screen 440 in a state in which multiple images are displayed in the image viewer according to this embodiment. FIG. 11A is a diagram that illustrates a search result screen 453 in a single image display state of the image viewer according to this embodiment, and FIG. 11B is a diagram that illustrates a search result screen 466 in a multiple image display state of the image viewer according to this embodiment. FIG. 12A is a diagram that illustrates an image display screen 530 in the single image display state of the image viewer according to this embodiment, and FIG. 12B is a diagram that illustrates an image display screen 550 in the multiple image display state of the image viewer according to this embodiment. FIG. 15 is a flowchart in a case where the image viewer according to the third embodiment is used in which user operations are not represented and is a flowchart acquired by excluding steps of user inputs from FIG. 4. In this embodiment, each process of FIG. 15 may be automatically performed at predetermined timing, or at least one process may be performed semi-automatically at the timing when there is a user input.

First, in Step S401, the PC 10 starts up the Web browser 11 in accordance with a user's instruction. Regarding the start-up of the Web browser, a browser that is designated in advance may be automatically started up based on a link installed in an external system such as an electronic clinical record system. In Step S402, the Web browser 11 of the PC 10 transmits the URL of a Web page 430 of the image viewer and a generation request signal to the Web server 21. The Web server 21 generates the Web page 430 of the image viewer according to the received URL. In Step S403, the Web server 21 transmits an examination item list request signal to the request processing section 23. The request processing section 23 acquires the examination item list from the general-purpose information database 60 and transmits the acquired examination item list to the Web server 21.

In Step S404, the Web server 21 sets the received examination item list in the examination item input section 433 of the Web page 430 of the image viewer generated in Step S402 and forms a state in which the user can select one examination item included in the examination item list. Here, the examination item, for example, is a keyword representing the type of examination or the type of image data such as a photograph during an operation, a pathology photograph, an echographic examination image, or an X-ray photograph. The Web server 21 transmits the generated Web page 430 of the image viewer to the Web browser 11 of the PC 10, and the Web browser 11 of the PC 10 displays the Web page 430 of the image viewer.

In Step S405, the user may input the ID of the patient to a patient ID input section 431 of the Web page 430 of the image viewer. In Step S406, the user may input an examination period to an examination period input section 432 of the Web page 430 of the image viewer. In Step S407, the user may input an examination item to the examination item input section 433 of the Web page 430 of the image viewer.

In Step S408, when the user presses a search button 434 of the Web page 430 of the image viewer, the Web browser 11 of the PC 10 transmits a search condition and a search request signal to the request processing section 23 through the Web server 21. Here, the search condition is the ID of a patient in a case where the patient's ID is input in Step S405, an input examination period in a case where the examination period is input in Step S406, and an examination item in a case where the examination item is input in Step S407. In Step S4081, in a case where there is no search condition, the process is returned to a search condition inputting process (Step S405, Step S406, or Step S407). The request processing section 23 acquires an image information group that matches the received search condition from the image database 24. In Step S4082, in a case where no image information is acquired, the process is returned to Step S405, S406, or S407.

In Step S409, the request processing section 23 counts the number of pieces of image information in which the examination ID overlaps each other from the image information group acquired in Step S408 and adds the number as an image data number of the examination ID to the examination information. At that time, in a case where the image data number has already been included in the image information, the image data number is overwritten. In addition, until there is no overlap of the examination ID, the image information of which the examination ID overlaps each other is removed one by one.

In Step S410, the image information group generated in Step S409 is transmitted to the Web server 21. The Web server 21 generates an examination list display section 458 on the Web page 453 of the image viewer based on the received image information group. The examination list display section 458 is configured by one or more examination list items, and one examination list item corresponds to one piece of information that has been received. A representative thumbnail image 459 and examination information 460 are attached to the examination list item. The representative thumbnail image 459 is acquired by generating a thumbnail image from the file path of the image data included in the image information corresponding to the examination list item. The examination information 460 includes the name of a patient, examination date and time, an examination item, and an image data number added in Step S409 that are included in the image information corresponding to the examination list item. In addition, the examination information may be only stored in a code of the Web page 453 of the image viewer without being displayed on the user interface. The Web server 21 transmits the generated Web page 453 of the image viewer to the Web browser 11 of the PC 10, and the Web browser 11 displays the Web page 453 of the image viewer.

In Step S411, when the user selects an arbitrary list item from the examination list display section 458, the Web browser 11 transmits an examination ID included in the image information corresponding to the examination list item and an image list generating request signal to the request processing section 23 through the Web server 21. Then, the request processing section 23 acquires an image information group including the received examination ID from the image database and transmits the acquired image information group to the Web server 21 of the image management server 20.

In Step S412, the Web server 21 generates an image list display section 535 on the Web page 530 of the image viewer based on the received image information group. Here, the image list display section 535 is configured by one or more image list items, and one image list item corresponds to one image information piece that has been received. A thumbnail image and image information are attached to the image list item. The image thumbnail is acquired by generating a thumbnail image from the file path of the image data included in the image information corresponding to the image list item. The image information is information included in the image information corresponding to the image list item, for example, photography date and time, a comment, and an image URL. In addition, the information included in the image information is selected to be only stored in the code of the Web page of the image viewer, and there may be information that is not displayed on the user interface. In a case where a flag indicating the completion of deletion is added to the image information, the image list item is not added.

In Step S413, when the user selects an arbitrary examination list item from the image list display section 535, the Web browser 11 of the PC 10 refers to the URL of the image included in the image information and displays the image data on the image display section 542 of the Web page of the image viewer. In addition, in a case where the image processing information or the image additional information is included in the image information, the image data is displayed in a state in which the image data is processed based on the information.

In Step S414, the image data displayed on the image display section may be enlarged or reduced in accordance with a user's specific operation. As a method of the operation, for example, an operation of a wheel on the image display section 542 using a mouse to which the wheel is attached or an operation of pressing a key in the keyboard may be employed.

In Step S415, the user may move a display area of the image data displayed on the image display section 542. As a method of the operation, a drag operation on the image display section or an operation of a cross-key in the keyboard may be employed.

In Step S416, the user may add or overwrite the image processing information or the image additional information to the image information by performing an editing operation of the image data that is currently displayed on the image display section 542 by pressing an arbitrary image editing button included in the image editing button group 541. When the editing operation is performed, a result of the editing operation is displayed on the image display section. Here, the editing operation is an operation of generating image processing information by rotating an image, performing vertical reversal/horizontal reversal of an image, selecting and trimming an arbitrary rectangular area in an image, adjusting colors, directly writing a graphic or a text in the image data or an operation of generating the image additional information by adding a comment to the image data or adding information used for displaying a graphic or a text to be superimposed on the image. In addition, the image data displayed on the image display section 465 is image data that is temporarily generated, for which the image editing has been completed, on which the image processing information or the image additional information is reflected. When one editing operation is completed, the Web page 530 of the image viewer transmits new image information in which the image processing information or the image additional information is updated and an image information updating request signal to the Web server 21. In addition, the Web page 530 of the image viewer overwrites image information of the image list item corresponding to the image data that is currently displayed with the above-described new image information.

In Step S417, the Web server 21 of the image management server 20 transmits the image information and an image update request signal that have been received to the request processing section 23. The request processing section 23 overwrites corresponding image information included in the image database 24 with the received image information.

In Step S418, the user may display one image data piece on the image display section 439 by pressing a single image displaying button 435. In Step S419, the user may display two image data pieces on image display sections 449 and 452 by pressing a multiple image displaying button 446. In addition, a multiple image display may be used for aligning and comparing photograph records with each other so as to check a temporal change in lacerations due to treatment or the like, which is important in medical institutions. In addition, when two or more pieces of image data are displayed, the frame of the image display section is highlighted in the display, and the operation of an image checking and editing process (Steps S414, S415, and S416 to S417) continued from the image list item selecting process (Step S413) is performed for the image display section that is highlighted in the display. In addition, the number of image display sections at the time of pressing a plurality of image displaying buttons may be two or more. Here, the single image displaying button 445 represents a state of not being pressed, and when the single image displaying button 445 is pressed, the display form thereof is changed as that of the single image displaying button 435. In accordance with this, the multiple image displaying button 436 changes the display form thereof as that of the multiple image displaying button 446.

In Step S420, when the user clicks the image display section of which the frame is not highlighted in the display, the highlighted display of the frame of the image display section, of which the frame is highlighted in the display, disappears, and the frame of the image display section that has been clicked as above is highlighted in the display. In Step S4201, when the user ends the operation of the image viewer, in Step S421, by ending the operation of the Web browser, the operation of the image viewer also ends. When the user does not end the operation of the image viewer, the process is returned to right after the process of Step S404.

Fourth Embodiment

Image Uploader

Figure 8A:
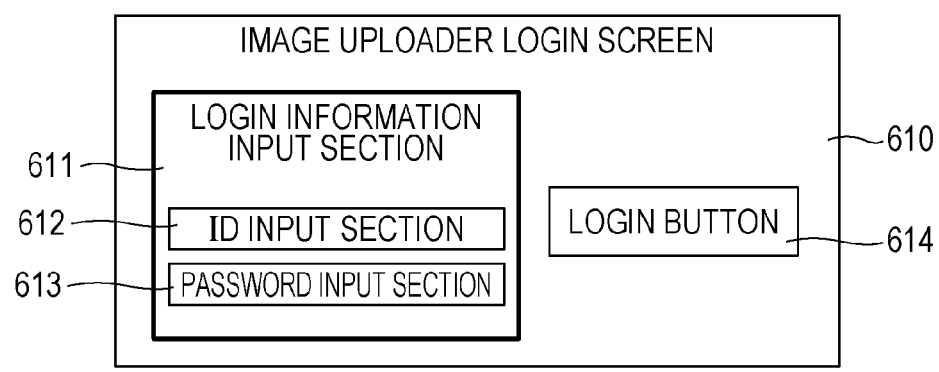
Figure 16:
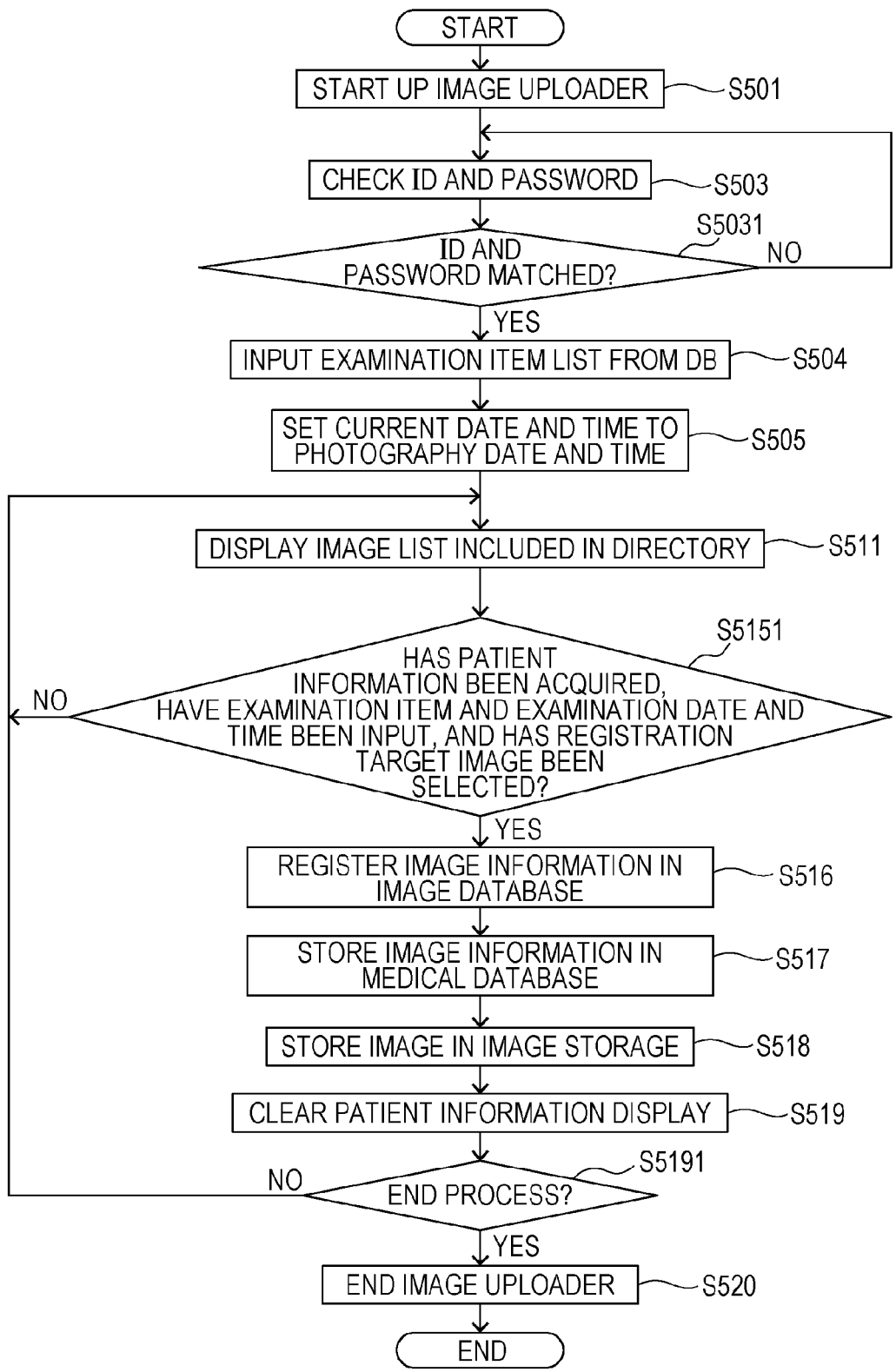
FIG. 16 is a flowchart in a case where the image uploader according to the fourth embodiment is used in which user operations are not represented.

Next, the flow in a case where an image uploader module according to a fourth embodiment is used will be described with reference to FIGS. 5, 8A, 8B and 16. FIG. 5 is a flowchart in a case where the image uploader according to this embodiment is used. FIG. 8A is a diagram that illustrates a login screen of the image uploader according to this embodiment, and FIG. 8B is a diagram that illustrates an image registering screen of the image uploader according to this embodiment. In addition, FIG. 16 is a flowchart in a case where the image uploader according to this embodiment is used in which user operations are not represented and is a flowchart acquired by excluding steps of user inputs from FIG. 5. In this embodiment, each process of FIG. 16 may be automatically performed at predetermined timing, or at least one process may be performed semi-automatically at the timing when there is a user input.

First, in Step S501, the image uploader is started up in accordance with a user's input. Next, in Step S502, an ID is input to an ID input section 612 of a login information input section 611 on the login screen 610 of the image uploader, a password is input to a password input section 613, and a login button 614 is pressed in accordance with user's inputs.

In Step S503, the image uploader transmits a login request signal to a request processing section 23 together with the user's ID and the user's password. At this time, the request processing section 23 searches the medical database 70 for the received user's ID. Here, the request processing section 23 determines whether or not the user's ID is present in a medical database 70. In a case where the user's ID is not present therein, the request processing section 23 transmits a login failure signal to the image uploader. On the other hand in a case where the user's ID is present therein, in Step S5031, the request processing section 23 checks whether or not a password, which is included in the medical database 70, corresponding to the user's ID matches the received password. In a case where the passwords match each other, the request processing section 23 transmits a login success signal to the image uploader. On the other hand, in a case where the passwords do not match each other, the request processing section 23 transmits a login failure signal to the image uploader. In a case where the image uploader receives a login failure signal, the process is returned to Step S502. In addition, when the image uploader receives the login success signal, the image uploader transits to the image registering screen 620, and the process proceeds to Step S504.

In Step S504, the image uploader transmits an examination item list request signal to the request processing section 23. The request processing section 23 acquires the examination item list from the general-purpose information database 60 and transmits the acquired examination item list to the image uploader. The image uploader sets the received examination item list in an examination item input section 623 and forms a state in which the user can select one examination item from the examination item list. Here, the examination item, for example, is a keyword representing the type of examination or the type of image data such as a photograph during an operation, a pathology photograph, an echographic examination image, or an X-ray photograph.

In Step S505, the image uploader acquires the current date and time of the PC 10 that operates the image uploader and inputs the date and time to an examination date and time input section 624 as a default value. In Step S506, the ID of a patient is input to a patient ID input section in accordance with a user's instruction.

In Step S507, the image uploader checks that the ID of the patient input to the patient ID input section satisfies the character string rule of a patient's ID and transmits the received ID of the patient and a patient information acquiring request signal to the request processing section 23. The request processing section 23 searches for the received ID of the patient so as to determine whether the received ID of the patient is present in the medical database 70. In a case where the received ID of the patient is not present therein, the request processing section 23 transmits a patient ID search failure signal to the image uploader. On the other hand, in a case where the received ID of the patient is present therein, the request processing section 23 transmits patient information, which is included in the medical database 70, corresponding to the ID of the patient to the image uploader. The patient information, for example, is information relating to a patient such as the name and the ID of a patient, the gender of a patient, date of birth of a patient, and the age of a patient. The image uploader displays the received patient information on a patient information display section.

In Step S508, the user selects an examination item at the examination item input section 623. In Step S509, the user inputs an examination date and time in the examination date and time input section 624. However, in a case where one or more pieces of the registration target image data including date and time information are included in the registration target image data group selected in Step S514, the user may select to employ the oldest date and time information of date and time information as examination date and time. In such a case, the user operates a toggle button 625 used for using date and time included in the registration target image data group to be turned on.

In addition, in Step S510, the user inputs an image storing directory path to an image storing directory path input section 627. As an inputting method thereof, for example, a directory path may be automatically input by using a directory path acquiring function using a directory selecting dialog or a directory path acquiring function, which is a function of the operating system, executed by performing drag and drop of image data or a directory in the image uploader. The image uploader inputs the image data group stored in the image storing directory path input to an image storing directory path input section 627 to a management memory of the of the image uploader. The image uploader acquires a thumbnail image and image information by analyzing each input image data. Here, the thumbnail image is a reduced image of the image data. In addition, the image information is information of image data such as an image information ID used for identifying image information, the name and the file size of the photographed image data, the number of pixels in a horizontal width, the number of pixels in the height, generation date and time, photography date and time, update date and time, image rotation information, and an image acquiring device ID. Here, the thumbnail image is a rotated image on which the image rotation information is reflected.

In Step S511, the image uploader adds a set of the thumbnail image of each image data and the image information, which are input in Step S510, as an image list item of the image list display section. In addition, a check box 629 is attached to each item, and the user operates the selection of registration target image data in Step S514 by using the check box 629.

In Step S512, the user may select an arbitrary image list item of the image list display section 628 and display the thumbnail image of the image list item selected in the image display section 633 and the image data, which is input in Step S510, that is the source of the image information. The image data that is displayed is the rotated image data, which is temporarily generated, on which the image rotation information acquired in Step S510 is reflected.

In Step S513, the image data displayed on the image display section 633 may be enlarged or reduced in accordance with a user's specific operation. As a method of the operation, for example, an operation of a wheel using a mouse to which the wheel is attached or an operation of pressing a key in the keyboard may be employed. In addition, the user may move a display area of the image displayed on the image display section 633. As a method of the operation, a drag operation of the image or an operation of a cross-key in the keyboard may be employed. Furthermore, the user may add the image processing information or the image additional information to the image information by performing an editing operation of the image data that is currently displayed on the image display section 633 by pressing an arbitrary image editing button included in the image editing button group 632. When the editing operation is performed, a result of the editing operation is displayed on the image display section. Here, the editing operation is an operation of generating image processing information by rotating an image, performing vertical reversal/horizontal reversal of an image, selecting and trimming an arbitrary rectangular area in an image, adjusting colors, directly writing a graphic or a text in the image data or an operation of generating the image additional information by adding a comment to the image data or adding information used for displaying a graphic or a text to be superimposed on the image. In addition, the image data displayed on the image display section 633 and the thumbnail image displayed in the image list display section are image data that is temporarily generated, for which the image editing has been completed, on which the image processing information or the image additional information is reflected. In other words, there is no influence such as rewriting of the source image data input in Step S510.

In Step S514, the user may select registration target image data by operating a check box 629 attached to an arbitrary image list item of the image list display section 628. Here, the registration target image data is image data, which is input in Step S510 and is the source of the image information corresponding to the image list item to which the checked check box is attached.

In Step S515, by the user pressing a registration button 626, the image uploader copies the registration target image data (an image checked in the check box) to an image storage 25, and an image registering process is started in which information relating to the registration target image data is registered in the image database 24. In Step S5151, the image uploader determines whether patient information has been acquired in Step S507, an examination item has been selected in Step S508, the examination date and time has been input in Step S509, and one or more pieces of registration target image data have been selected in Step S514. In addition, in a case where the toggle button 625 used for using date and time included in the registration target image data is turned on in Step S509, the image uploader selects registration target image data having the oldest date and time information from among the registration target image data selected in Step S514 and employs the date and time as the examination date and time. In such a case, the examination date and time is assumed to have been input. In a case where there is no registration target image data having date and time information, the image uploader presents a message indicating that there is no registration target image data having date and time information to the user, the registration process is stopped, and the process is returned to right after the process of Step S505.

In Step S516, an image information group of the registration target image data group and an image information registering request signal are transmitted to the request processing section 23. In a case where the image processing information generated in Step S513 is included in the registration target image information, a copy of the registration target image data corresponding to each registration target image information may be processed based on the corresponding image processing information, and the image processing information may be deleted from the registration target image information. In addition, in a case where the image rotation information is included in the registration target image information, the registration target image data corresponding to each registration target image information may be rotated based on the corresponding image rotation information, and the image rotation information may be deleted from the registration target image information. In addition, the request processing section 23 registers the received registration target image information group in the image database. Furthermore, the request processing section 23, in Step S518, additionally registers image information of each registration target image data in the image management server 20, which is recorded by an FTP server 22, in the registration target image information. Here, the image information of the image management server 20, for example, is information relating to the image data such as a file path of the registration target image data in the image storage 25 and an URL used for displaying the image data. In addition, the request processing section 23 additionally registers a unique examination ID that is the same for all the registered registration target image information group.

In Step S517, the request processing section 23 registers the management image information, which has been registered in the image database 24 in Step S516, also in the medical database 70. The registered management information is used by an external system such as an electronic clinical record system, and, for example, by clicking the URL installed to the user interface of the electronic clinical record system, the image data recorded in Step S518 can be referred to. In Step S518, the image uploader transmits a copy of the registration target image data group and thumbnail images corresponding thereto to the FTP server 22. The FTP server 22 records a copy of the registration target image data group that has been received in the image storage. In Step S519, when the user continue to perform the registration process, in order not to register image data in association with the ID of another patient due to an error in the image data, the image uploader blanks the ID of the patient input to the patient ID input section 621 and blanks the patient information display section 622. In Step S5191, in a case where the image uploader ends such as a case where there is no image data to be registered further, the image uploader ends in Step S520.

Fifth Embodiment

Automatic Deletion of Image Data

Figure 6:
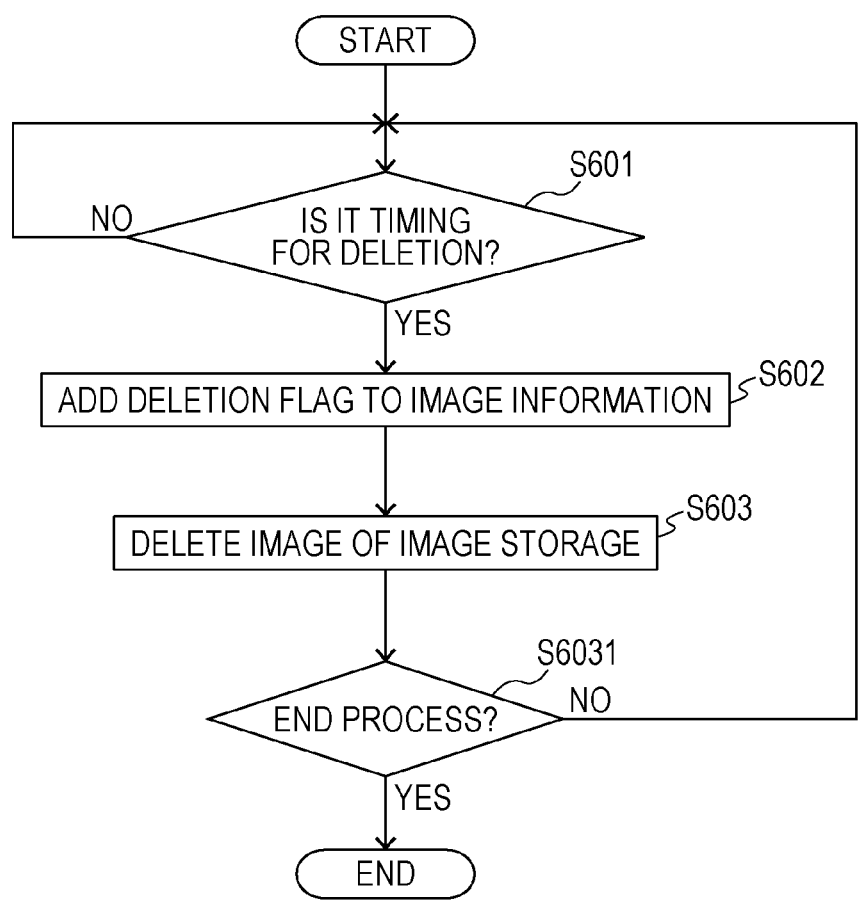
FIG. 6 is a flowchart that illustrates a function for automatically deleting image data according to a fifth embodiment.

Next, a flow of automatically deleting image data according to a fifth embodiment will be described with reference to FIG. 6. FIG. 6 is a flowchart that illustrates a function for automatically deleting image data according to this embodiment.

Here, the automatic deletion of the image data is one function of the file monitoring section 54. More specifically, the automatic deletion of the image data is a function in which image data stored in the image storage 56 but not registered in the image management server 20 is regarded as unnecessary data and is removed. By deleting the image data, the remaining capacity of the image storage 56 is saved, and risk is reduced against the case of the leak of information of the image data.

First, in Step S601, a determination section of the file monitoring section 54 determines whether it is timing for deletion, for example, predetermined time every day. Next, in the case of the timing for deletion, in Step S602, the file monitoring section 54 additionally registers a deletion flag in image information having transmission date and time, which is included in the image information, to be different from the current date and time by a predetermined period by referring to the image database 55. In Step S603, the file monitoring section 54 deletes image data and thumbnail images corresponding to the image information to which the deletion flags have been added in Step S602 from the image storage 56. The timing for deletion is registered by the user in advance and is preferably configured so as to be changeable on the initial setting screen or the like.

In addition, while the above-described operation is continued while the power of the server is turned on, it may be determined whether or not the power is turned off in Step S6031. At this time, in a case where the power of the server is determined to have been turned off by the determination section, this flow ends.

Sixth Embodiment

Barcode Recognition Function

Next, a barcode recognition function according to a sixth embodiment will be described. In Steps S303, S311, S405, and S506, the process of inputting the ID of a user or a patient may be replaced with the barcode recognition function. In addition, the barcode recognition function may be realized by a barcode reader function built in the mobile terminal 30 or by photographing a barcode using the wireless digital camera 40, recognizing the barcode from the photographed image data to be decoded into the ID of a patient in Step S330 illustrated in FIG. 13, and transmitting the ID of the patient to the mobile terminal 30 using the file monitoring section 54. Particularly, in the facilities of recent medical institutions, a wristband acquired by printing a barcode of the ID of each inpatient is frequently generated and attached to the patient during hospitalization. Accordingly, an environment in which the operation of inputting the ID of each patient to the mobile terminal 30 can be omitted increases by a barcode recognition function. In such a case, it is preferable that the function of the mobile terminal 30 and the function of the wireless digital camera 40 be integrally configured, and, for example, it is preferable that the mobile terminal 30 also has the function of the wireless digital camera 40.

Seventh Embodiment

Addition of Information Representing Type of Image Data to Image Data

Next, the process of adding information representing the type of image data to the image data according to a seventh embodiment will be described. An analysis section of the file monitoring section 54 analyzes received image data in Step S330 illustrated in FIG. 13. In a case where photography of not a human body such as an affected part but a paper document or a white board is analyzed by the analysis section, information representing that the image data is a document may be added to the image data. In the facilities of medical institutions, while many paper documents accompanied with patients are generated, and, in many cases, such documents are digitalized by using an image scanner and are stored, the wireless digital camera 40 can be used instead of the image scanner by performing the above-described process. Generally, since a wireless digital camera has portability superior to that of an image scanner, documents can be scanned at many places. In addition, since the image data can be registered in association with the ID of a patient in accordance with this embodiment, it can be checked using an image viewer whether all the documents such as agreements are included by searching for documents using the ID of the patient. In addition, in the analysis process of Step S330, by detecting and trimming a document area from the photographed image data, an unnecessary area other than the document is removed, whereby the use value as a replacement of an image scanner increases. In addition, in the analysis process of Step S330, by recognizing the document type of the photographed image data, for example, a first document, a second document, or the like and adding the document type to the image information, the document type can be checked using the image information 537 provided on the image viewer screen 530 or the image viewer screen 550 when an image is read in the image viewer. In addition, the determination section of the file monitoring section 54 may determine whether or not a plurality of types of documents registered in advance are included. At this time, in a case where the documents are not included, the Web browser 31 may have a display form representing an insufficient document. From this, the user can easily recognize an insufficient document. Here, the analysis section or the determination section may be configured as a functional unit other than the file monitoring section 54.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-091250, filed Apr. 12, 2012, and Japanese Patent Application No. 2013-030899, filed Feb. 20, 2013, which are hereby incorporated by reference herein in their entirety.

What is claimed is:

1. A medical support system in which a plurality of photography apparatuses and a portable-type apparatus including a display unit are communicably connected to a server,
wherein the portable-type apparatus comprises:
   a selection unit that selects one of the plurality of photography apparatuses;
   a photographer ID input unit that inputs a photographer ID that is an ID of a photographer photographing a subject using the selected photography apparatus; and
   a first transmission unit that transmits the input photographer ID to the server,
wherein the selected photography apparatus further comprises a second transmission unit that transmits image data of the subject photographed by the selected photography apparatus to the server, and
the server comprises:
   a receiving unit that receives the transmitted photographer ID and the transmitted image data; and
   a recording unit that records the received photographer ID and the received image data in association with each other,
   wherein, in a case where image data of the subject photographed by a different photography apparatus other than the selected photography apparatus is received, the recording unit does not record the received image data of the subject photographed by the different photography apparatus and the received photographer ID in association with each other.

2. The medical support system according to claim 1, further comprising a display control unit that displays, on the display unit, an image based on the image data recorded in association with the photographer ID by the recording unit in a case where the photographer ID is input.

3. The medical support system according to claim 2,
wherein the portable-type apparatus further comprises a subject ID input unit that inputs a subject ID that is an ID of the subject accompanied with the image data, and
wherein, in a case where the subject ID is input, the display control unit displays, on the display unit, a display form that is based on data relating to the subject through the server.

4. The medical support system according to claim 2,
wherein the server adds information representing a type of the recorded image data to the image data, and
in a case where the image data of a predetermined type is not recorded, the display control unit displays, on the display unit, a display form representing the type of the image data that is not recorded.

5. The medical support system according to claim 1, wherein the server further comprises a recording control unit that deletes, from the recording unit, the recorded image data and a thumbnail image that is based on the image data after an elapse of a predetermined period from when photography is performed by the photography apparatus.

6. The medical support system according to claim 5, wherein the recording control unit adds a deletion flag to the recorded image data after the predetermined period elapses from when photography is performed by the photography apparatus and deletes, from the recording unit, the image data to which the deletion flag is added and the thumbnail image that is based on the image data at predetermined time every day.

7. The medical support system according to claim 5, wherein the portable-type apparatus further comprises a registration unit that registers the recorded image data, and the recording control unit does not delete the data registered by the registration unit after an elapse of a predetermined period.

8. A medical support system in which a plurality of photography apparatuses and a portable-type apparatus including a display unit are communicably connected to a server, wherein the portable-type apparatus comprises:
an input unit that inputs a photography apparatus ID that is an ID of one of the plurality of photography apparatuses;
a subject ID input unit that inputs a subject ID that is an ID of the subject; and
a first transmission unit that transmits the input photography apparatus ID and the input subject ID to the server,
the photography apparatus having the input photography apparatus ID comprises a second transmission unit that transmits image data of a subject photographed by the photography apparatus having the input photography apparatus ID to the server, and
the server comprises:
a receiving unit that receives the transmitted photography apparatus ID, the transmitted subject ID, and the transmitted image data;
a recording unit that records the received subject ID and the received image data in association with each other; and
a third transmission unit that transmits data relating to the subject to the portable-type apparatus,
wherein, in a case where image data of the subject photographed by a different photography apparatus other than the photography apparatus is received, the recording unit does not record the received image data of the subject photographed by the different photography apparatus and the received subject ID in association with each other.

9. A medical support system in which a photography apparatus and a portable-type apparatus including a display unit are communicably connected to a server,
wherein the portable-type apparatus comprises:
a photographer ID input unit that inputs a photographer ID that is an ID of a photographer photographing a subject using the photography apparatus; and
a first transmission unit that transmits the input photographer ID to the server,
the photography apparatus further comprises a second transmission unit that transmits image data of the subject photographed by the photography apparatus to the server, and
the server comprises:
a receiving unit that receives the transmitted photographer ID and the transmitted image data; and
a recording unit that records the received photographer ID and the received image data in association with each other,
wherein, in a case where image data of the subject photographed by a different photography apparatus other than the photography apparatus is received, the recording unit does not record the received image data of the subject photographed by the different photography apparatus and the received photographer ID in association with each other.

10. A non-transitory computer-readable medium having stored thereon a program that causes a computer to execute each function of the medical support system according to claim 1.

11. A non-transitory computer-readable medium having stored thereon a program that causes a computer to execute each function of the medical support system according to claim 8.

12. A non-transitory computer-readable medium having stored thereon a program that causes a computer to execute each function of the medical support system according to claim 9.

13. A medical support system in which a photography apparatus and a portable-type apparatus including a display unit are communicably connected to a server,
wherein the portable-type apparatus comprises:
a photographer ID input unit that inputs a photographer ID that is an ID of a photographer photographing a subject using the photography apparatus;
a subject ID input unit that inputs a subject ID that is an ID of the subject; and
a first transmission unit that transmits the input photographer ID and the input subject ID to the server,
the photography apparatus further comprises a second transmission unit that transmits image data of the subject photographed by the photography apparatus to the server, and
the server comprises:
a receiving unit that receives the transmitted photographer ID, the transmitted subject ID, and the transmitted image data;
a recording unit that records the received photographer ID, the received subject ID, and the received image data in association with each other; and
a third transmission unit that transmits data relating to the subject to the portable-type apparatus,
wherein, in a case where image data of the subject photographed by a different photography apparatus other than the photography apparatus is received, the recording unit does not record the received image data of the subject photographed by the different photography apparatus, the received photographer ID, and the received subject ID in association with each other.

14. A non-transitory computer-readable medium having stored thereon a program that causes a computer to execute each function of the medical support system according to claim 13.

15. The medical support system according to claim 8,
wherein the portable-type apparatus further comprises a display control unit configured to cause the display unit to display a display form corresponding to the data relating to the subject,
wherein the third transmission unit is configured to transmit new image data generated based on the received image data to the portable-type apparatus, and
wherein the display control unit is configured to cause the display unit to display the display form corresponding to the data relating to the subject and an image corresponding to the new image data on a same screen of the display unit.

16. The medical support system according to claim 13,
wherein the portable-type apparatus further comprises a display control unit configured to cause the display unit to display a display form corresponding to the data relating to the subject,
wherein the third transmission unit is configured to transmit new image data generated based on the received image data to the portable-type apparatus, and
wherein the display control unit is configured to cause the display unit to display the display form corresponding to the data relating to the subject and an image corresponding to the new image data on a same screen of the display unit.

17. The medical support system according to claim 8,
wherein the portable-type apparatus further comprises a display control unit configured to cause the display unit to display a display form corresponding to the data relating to the subject,
wherein the third transmission unit is configured to transmit at least a part of the received image data to the portable-type apparatus, and
wherein the display control unit is configured to cause the display unit to display the display form corresponding to the data relating to the subject and an image corresponding to the at least a part of the received image data on a same screen of the display unit.

18. The medical support system according to claim 13,
wherein the portable-type apparatus further comprises a display control unit configured to cause the display unit to display a display form corresponding to the data relating to the subject,
wherein the third transmission unit is configured to transmit at least a part of the received image data to the portable-type apparatus, and
wherein the display control unit is configured to cause the display unit to display the display form corresponding to the data relating to the subject and an image corresponding to the at least a part of the received image data on a same screen of the display unit.

19. The medical support system according to claim 1,
wherein the server further comprises a third transmission unit configured to transmit data relating to the subject and new image data generated based on the received image data to the portable-type apparatus, and
wherein the portable-type apparatus further comprises a display control unit configured to cause the display unit to display a display form corresponding to the data relating to the subject and an image corresponding to the new image data on a same screen of the display unit.

20. The medical support system according to claim 9,
wherein the server further comprises a third transmission unit configured to transmit data relating to the subject and new image data generated based on the received image data to the portable-type apparatus, and
wherein the portable-type apparatus further comprises a display control unit configured to cause the display unit to display a display form corresponding to the data relating to the subject and an image corresponding to the new image data on a same screen of the display unit.

21. The medical support system according to claim 1,
wherein the server further comprises a third transmission unit configured to transmit data relating to the subject and at least a part of the received image data to the portable-type apparatus, and
wherein the portable-type apparatus further comprises a display control unit configured to cause the display unit to display a display form corresponding to the data relating to the subject and an image corresponding to the at least part of the received image data on a same screen of the display unit.

22. The medical support system according to claim 9,
wherein the server further comprises a third transmission unit configured to transmit data relating to the subject and at least a part of the received image data to the portable-type apparatus, and
wherein the portable-type apparatus further comprises a display control unit configured to cause the display unit to display a display form corresponding to the data relating to the subject and an image corresponding to the at least part of the received image data on a same screen of the display unit.

23. The medical support system according to claim 1,
wherein the server further comprises a third transmission unit configured to transmit information for referring to data recorded in association to an external system, and
wherein the data recorded in association is referred to via a user interface of the external system.

24. The medical support system according to claim 9,
wherein the server further comprises a third transmission unit configured to transmit information for referring to data recorded in association to an external system, and
wherein the data recorded in association is referred to via a user interface of the external system.

25. The medical support system according to claim 8,
wherein the third transmission unit is configured to transmit information for referring to data recorded in association to an external system, and
wherein the data recorded in association is referred to via a user interface of the external system.

26. The medical support system according to claim 13,
wherein the third transmission unit is configured to transmit information for referring to data recorded in association to an external system, and
wherein the data recorded in association is referred to via a user interface of the external system.

27. The medical support system according to claim 23, wherein the external system is an electronic clinical record system.

28. The medical support system according to claim 24, wherein the external system is an electronic clinical record system.

29. The medical support system according to claim 25, wherein the external system is an electronic clinical record system.

30. The medical support system according to claim 26, wherein the external system is an electronic clinical record system.

* * * * *